US005571703A

United States Patent [19]
Chieffalo et al.

[11] Patent Number: 5,571,703
[45] Date of Patent: *Nov. 5, 1996

[54] MUNICIPAL SOLID WASTE PROCESSING FACILITY AND COMMERCIAL ETHANOL PRODUCTION PROCESS

[75] Inventors: Rodger Chieffalo, Birmingham, Ala.; George R. Lightsey, Starkville, Miss.

[73] Assignee: Controlled Environmental Systems Corporation, Birmingham, Ala.

[*] Notice: The term of this patent shall not extend beyond the expiration date of Pat. No. 5,407,817.

[21] Appl. No.: 422,585

[22] Filed: Apr. 14, 1995

Related U.S. Application Data

[63] Continuation-in-part of Ser. No. 351,017, Dec. 7, 1994, abandoned, which is a continuation-in-part of Ser. No. 291,045, Aug. 12, 1994, Pat. No. 5,407,817, which is a continuation of Ser. No. 172,202, Dec. 23, 1993.

[51] Int. Cl.$^6$ ............................... C12P 19/02; C12P 7/10
[52] U.S. Cl. ........................ 435/105; 435/161; 435/163; 435/165; 435/171; 435/262; 426/11; 426/14
[58] Field of Search ................................ 435/165, 161, 435/163, 171, 262, 105; 426/11, 14

[56] References Cited

U.S. PATENT DOCUMENTS

| | | | |
|---|---|---|---|
| 1,888,935 | 11/1932 | Placek . | |
| 2,348,451 | 5/1944 | Christensen . | |
| 2,890,138 | 6/1959 | Smith et al. . | |
| 3,972,775 | 8/1976 | Wilke et al. | 195/33 |
| 3,990,945 | 11/1976 | Huff et al. | 195/33 |
| 4,009,075 | 2/1977 | Hoge | 195/33 |
| 4,025,356 | 5/1977 | Nyman et al. | 127/1 |
| 4,063,903 | 12/1977 | Beningson et al. | 44/2 |
| 4,069,145 | 1/1978 | Sommer, Jr. et al. | 209/212 |
| 4,093,516 | 6/1978 | Lang | 195/27 |
| 4,094,740 | 6/1978 | Lang | 195/27 |
| 4,110,281 | 8/1978 | Dreer | 523/129 |
| 4,237,226 | 12/1980 | Grethlein | 435/99 |
| 4,242,455 | 12/1980 | Muller et al. | 435/162 |
| 4,243,750 | 1/1981 | Muller et al. | 435/162 |
| 4,266,027 | 5/1981 | Muller et al. | 435/99 |
| 4,266,981 | 5/1981 | Tsao et al. | 127/37 |
| 4,287,303 | 9/1981 | Dahlberg et al. | 435/162 |
| 4,287,304 | 9/1981 | Muller et al. | 435/162 |
| 4,288,550 | 9/1981 | Ishida et al. | 435/167 |
| 4,289,540 | 9/1981 | Yong et al. | 127/33 |
| 4,321,328 | 3/1982 | Hoge | 435/165 |
| 4,326,036 | 4/1982 | Hayes | 435/161 |
| 4,330,625 | 5/1982 | Miller et al. | 435/161 |
| 4,341,353 | 7/1982 | Hamilton et al. | 241/24 |
| 4,342,830 | 8/1982 | Holloway | 435/167 |
| 4,350,766 | 9/1982 | Mehlberg | 435/161 |
| 4,384,897 | 5/1983 | Brink | 127/37 |
| 4,393,136 | 7/1983 | Cheethham | 435/161 |
| 4,400,469 | 8/1983 | Harris | 435/161 |
| 4,407,955 | 10/1983 | Muller et al. | 435/161 |
| 4,414,330 | 11/1983 | Zucker et al. | 435/93 |
| 4,421,856 | 12/1983 | Muller et al. | 435/161 |
| 4,432,805 | 2/1984 | Nuuttila et al. | 127/37 |
| 4,436,586 | 3/1984 | Elmore | 162/19 |
| 4,442,210 | 4/1984 | Dessau et al. | 435/161 |
| 4,490,469 | 12/1984 | Kirby et al. | 435/161 |
| 4,497,896 | 2/1985 | Assarsson et al. | 435/161 |
| 4,503,079 | 3/1985 | King et al. | 426/54 |
| 4,522,726 | 6/1985 | Berry et al. | 210/660 |
| 4,522,920 | 6/1985 | Thorsson et al. | 435/161 |
| 4,540,664 | 9/1985 | Johnson et al. | 435/99 |
| 4,541,530 | 9/1985 | Kenny et al. | 209/571 |
| 4,553,977 | 11/1985 | Fry | 44/1 D |
| 4,564,595 | 1/1986 | Neves | 435/163 |
| 4,578,353 | 3/1986 | Assarsson et al. | 435/161 |
| 4,612,286 | 9/1986 | Sherman et al. | 435/157 |
| 4,614,548 | 9/1986 | Cameron et al. | 127/40 |
| 4,617,270 | 10/1986 | Anderson et al. | 435/161 |
| 4,622,224 | 11/1986 | Owades | 426/16 |
| 4,650,689 | 3/1987 | Hedrick | 426/600 |
| 4,692,167 | 9/1987 | Levasseur | 44/2 |
| 4,709,903 | 5/1988 | Brink et al. | 127/1 |
| 4,749,651 | 6/1988 | Cvitas et al. | 435/99 |
| 4,752,579 | 6/1988 | Arena et al. | 435/99 |
| 4,764,276 | 8/1988 | Berry et al. | 210/264 |
| 4,874,134 | 10/1989 | Weins | 241/19 |
| 4,882,177 | 11/1989 | Dziondziak | 426/14 |
| 4,952,503 | 8/1990 | Granstedt | 435/161 |
| 4,952,504 | 8/1990 | Pavilon | 435/165 |
| 4,974,781 | 12/1990 | Placzek | 241/17 |
| 5,009,672 | 4/1991 | Ruffo et al. | 44/593 |
| 5,036,005 | 7/1991 | Tedder | 435/161 |
| 5,053,231 | 10/1991 | Riffkin et al. | 426/11 |
| 5,060,871 | 10/1991 | Brassinga et al. | 241/24 |
| 5,084,104 | 1/1992 | Heikkila et al. | 127/46.2 |
| 5,104,419 | 4/1992 | Funk | 48/209 |
| 5,135,861 | 8/1992 | Pavilon | 435/162 |
| 5,182,199 | 1/1993 | Hartley | 435/162 |
| 5,184,780 | 2/1993 | Wiens | 241/19 |
| 5,188,673 | 2/1993 | Clausen et al. | 127/37 |
| 5,198,074 | 3/1993 | Villavicencio et al. | 162/15 |
| 5,231,017 | 7/1993 | Lantero et al. | 435/161 |
| 5,258,293 | 11/1993 | Lynd et al. | 435/161 |
| 5,266,337 | 11/1993 | Barwald et al. | 426/15 |
| 5,407,817 | 4/1995 | Lightsey et al. | 435/165 |

OTHER PUBLICATIONS

"Ethanol From Cellulosic Residues and Crops: Annual Report", Tennessee Valley Authority (Oct. 1987).

"Integrated Fuel Alcohol Production Systems, Phase III: Experimental Facility Testing Report for the period of Jan. 15, 1984–Jan. 15, 1985", Tennessee Valley Authority, Office of Agricultural and Chemical Development.

Rossiter, Gordon, "ISEP A Moving Bed Contractor for Chromatographic Separations: Advanced Separation Technologies Incorporated", presented at the 4th Workshop on Preparative HPLC, Mar. 28–31, 1993, Salzburg, Austria.

*Primary Examiner*—Herbert J. Lilling
*Attorney, Agent, or Firm*—Sterne, Kessler, Goldstein & Fox, P.L.L.C.

[57] ABSTRACT

A method of processing waste is disclosed wherein the municipal solid waste is segregated and processed to recover reusable rubber, metal, plastic, glass and the remaining organic portion of the waste stream is used to make ethanol and other chemicals. One process utilizes a pretreatment step with dilute sulfuric acid to reduce the heavy metal content of the cellulosic component of the municipal solid waste which can inhibit the fermentation of the sugars obtained from such waste. In another, the heavy metal content of the cellulosic component of municipal solid waste is removed via an ionic exchange process, after hydrolysis with sulfuric acid. A process for an economical, energy efficient production of ethanol from municipal solid waste is also disclosed.

27 Claims, 1 Drawing Sheet

MUNICIPAL SOLID WASTE PROCESSING FACILITY AND COMMERCIAL ETHANOL PRODUCTION PROCESS

CROSS REFERENCE TO RELATED APPLICATIONS

This application is a continuation-in part of U.S. application Ser. No. 08/351,017, filed Dec. 7, 1994, now abandoned, which is a continuation-in part of U.S. application Ser. No. 08/291,045, filed Aug. 12, 1994, now U.S. Pat. No. 5,407,817, which is a continuation of application Ser. No. 08/172,202, filed Dec. 23, 1993, abandoned, the contents of each of which are fully incorporated by reference herein.

BACKGROUND OF THE INVENTION

1. Field of the Invention

The present invention relates to processes and facilities for the automated treatment of municipal solid waste (MSW) (land-filled or obtained directly from the municipality), sewage sludge, and scrap tires to remove and reclaim any usable materials and for producing commercial ethanol. The present invention further relates to a method for removing the heavy metals associated with the cellulosic component of the aforementioned solid waste.

2. Related Art

Generally, solid waste materials and waste sludge are disposed of by land fill and/or incineration. Environmental restrictions on both land fills and incinerators demand that an alternative solid waste solution be implemented. The public outcry concerning pollution caused by incinerators has halted construction of many new incinerator projects. The government, as a reaction to the problems associated with land fills, has mandated that recycling be employed to conserve natural resources and arrest the flow of solid waste materials into land fills.

A number of technologies have been developed to recover recyclable materials from solid waste, to produce fuel, and to produce commercially useful alcohols and gas. For example:

U.S. Pat. No. 5,198,074 discloses a process to produce ethanol from bamboo which involves chipping, shredding and washing of the bamboo, pressing to remove the water. The fiber is then prehydrolyzed with steam to give dissolved sugars and fermented to give ethanol.

U.S. Pat. No. 5,184,780 discloses a system for treating solid waste having one or more treatment lines for processing the solid waste to recover recyclable materials such as corrugated paper, ferrous metals, plastic products, paper and glass.

U.S. Pat. No. 5,135,861 discloses ethanol production from biomass which is hydrolyzed using the carbon dioxide produced from the fermentation reaction or the naturally occurring organic acids from citrus wastes as a catalyst.

U.S. Pat. No. 5,104,419 discloses a method of producing methanol from solid waste, for example, municipal solid waste, by partially oxidizing and combusting solid waste material, conducting the combustion gases, oxygen and carbon dioxide through the solid waste material, separating the less volatile components of the gas from the more volatile components, and reacting the more volatile components with carbon dioxide to form methanol.

U.S. Pat. No. 5,060,871 discloses methods of separating metal alloy particles by utilizing the difference in particle size, density and/or electric conductivity.

U.S. Pat. No. 5,036,005 discloses a method for the continuous fermentation production of fuel grade ethanol from a sugar, where the ethanol is removed in a solvent extraction column containing a solvent which is non-toxic to the fermentation microorganisms.

U.S. Pat. No. 5,009,672 discloses a process for the recycling and recovery of urban solid waste components by high pressure compression and screening as well as magnetic separation steps. The recovered putrescible organic component is then subjected to a process of anaerobic fermentation to give a biogas which can be used directly for the production of electric power.

U.S. Pat. No. 4,974,781 discloses a paper and plastic separation process which subjects the materials to moisture and heat to repulp the paper. The repulped materials are then separated from the non-pulpable materials and are then recycled, combusted or used as a feedstock in a chemical process.

U.S. Pat. No. 4,952,503 discloses a process for the continuous production of ethanol using a centrifugal separation step to remove the yeast.

U.S. Pat. No. 4,874,134 discloses a process for treating solid waste to recover recyclable materials such as corrugated paper, ferrous metals, non-ferrous metals, plastic products, paper and glass containers, as well as biodegradable waste materials which may be processed to give a compost. The bulky valuables, non-processable materials and redeemable materials are first recovered, a first ferrous metal fraction is then separated magnetically, the waste material is then shredded, a second ferrous metal fraction is then separated magnetically, and the paper fraction is then separated pneumatically to give a biodegradable fraction which can then be composted.

U.S. Pat. No. 4,692,167 discloses an apparatus for processing solid wastes for the production of a granule solid fuel by grinding, magnetically separating ferrous metals, screening, drying, gravity separation, cyclone separation, screening and press granulating.

U.S. Pat. No. 4,650,689 discloses a process for the preparation of ethanol from cellulosic materials by subjecting the cellulosic materials to a highly concentrated mineral acid gas such as HCl under pressure, and treatment with hot water to give a wort containing sugars which can be fermented.

U.S. Pat. No. 4,612,286 discloses a method for the acid hydrolysis of biomass having fermentable materials in a countercurrent diffusion treatment structure. Preferably, the acid is about 2 to 10% by volume sulfuric acid.

U.S. Pat. No. 4,553,977 discloses a method for separating solid waste components with a first trommel screen which removes aluminum cans to give an organics-rich fraction from which recyclable fiber products may be separated. Steel cans are removed by magnetic separation. The organics are isolated for use as a fuel, with or without pulping to recover paper pulp.

U.S. Pat. No. 4,541,530 discloses a method for separating metallic particles from non-metallic particles of processed solid waste by homogenizing and magnetically treating components of the waste to give a metallic concentrate, for example, an aluminum concentrate.

U.S. Pat. No. 4,384,897 discloses a method for treating biomass material by a two stage hydrolysis treatment, wherein in the first stage, the more easily hydrolyzed polysaccharides are depolymerized and in the second stage, the more difficultly depolymerizable polysaccharides are depolymerized. The biomass material may be subjected to a sensitization step between the first and the second hydrolysis stages by contact with molecular oxygen. The acids are neutralized with a base such as calcium carbonate or hydroxide to give a solution which is suitable for fermentation to give ethanol.

U.S. Pat. No. 4,341,353 discloses a method of recovering fuel and recyclables from refuse using disk screens and air classifiers.

U.S. Pat. No. 4,288,550 discloses a method of digesting garbage by anaerobic fermentation in the presence of ethanol producing yeast to directly convert starch to ethanol without a hydrolysis pretreatment and thereafter subjecting the product to methane producing anaerobic fermentation to give methane.

U.S. Pat. No. 4,069,145 discloses a method for separating particles of greater electrical conductivity from particles of lesser electrical conductivity in an electromagnetic eddy current separator apparatus.

U.S. Pat. No. 4,063,903 discloses an apparatus for the disposal of solid wastes by recovering the inorganic components and converting the organic component to a fuel or a fuel supplement. The shredded material is treated with an acid which is heated and dried and ground to give a finely divided fuel product.

SUMMARY OF THE INVENTION

It is an object of the present invention to provide an automated, efficient process for the treatment of municipal solid waste and sewage sludge, preferably in the form of sewage sludge cake, to recover any recyclable materials and to produce usable commercial ethanol.

It is the further object of the present invention to provide a method for the reclamation of existing land fills, thereby removing the future environmental impact of the old land fill.

It is also the further object of the present invention to provide a processing facility that will have, in effect, no adverse environmental impact.

The process for the continuous, automated treatment of municipal solid waste material and sewage sludge to remove and reclaim any usable materials and for producing commercial ethanol, comprises the following steps:

(a) delivering municipal solid waste to a processing facility in bulk;

(b) removing tires, bulk ferrous and non ferrous metals, plastic and glass from said waste to give a cellulosic component;

(c) shredding the cellulosic component obtained in step (b);

(d) treating the shredded cellulosic component and, optionally, sewage sludge with dilute (about 1 to 10%) sulfuric acid for about 0.25 to 4 hours at a temperature of about 40° to 100° C. to solubilize substantially the remaining heavy metals and give a soluble component and an insoluble component;

(e) removing the soluble component obtained in step (d) from the insoluble component;

(f) drying the insoluble component obtained in step (e);

(g) treating the dried insoluble component obtained in step (f) with about 1:1 concentrated sulfuric acid (about 70%) to insoluble component, by weight, to give a partially hydrolyzed mixture;

(h) diluting the partially hydrolyzed mixture obtained in step (g) with water at a temperature of about 80° C. to about 100° C. to give a solution containing, e.g. about 4 to 6 parts water to about 1 parts partially hydrolyzed material, by weight;

(i) agitating the diluted mixture obtained in step (h) for about 1 to 4 hours at about 80° C. to about 100° C. to give a digested material;

(j) removing the solids from the digested mixture obtained in step (i) to give a filtrate;

(k) separating the filtrate into an acid containing solution and a sugar containing solution;

(l) concentrating the sugar containing solution to about 12–14% sugar;

(m) adjusting the pH of the concentrated sugar containing solution obtained in step (l) to about 6;

(n) fermenting with yeast the solution obtained in step (m) at about 25° C. to about 36° C. to give a beer; and (o) recovering the ethanol from the beer.

The invention also relates to a method of removing trace heavy metals and chlorides from the cellulosic component of municipal solid waste, and/or sewage sludge comprising the following steps:

(a) shredding the cellulosic component of municipal solid waste;

(b) treating the shredded cellulosic component and, optionally, sewage sludge with dilute (about 1 to 10%) sulfuric acid for about 0.25 to 4 hours at a temperature of about 40° to 100° C. to solubilize the trace heavy metals, and give a soluble and an insoluble component;

(c) removing the soluble component obtained in step (b) from the insoluble component, to obtain an insoluble component having substantially no trace heavy metals.

The invention further relates to a method of producing ethanol and removing essentially all of the heavy metals and chlorides from the cellulosic component of municipal solid waste and/or sewage sludge comprising (a) shredding the cellulosic component of municipal solid waste;

(b) treating the shredded component obtained in step (a) and/or sewage sludge with about 1:1 concentrated sulfuric acid (about 70%) to solid component at about 30° to 80° C. to give a partially hydrolyzed mixture;

(c) diluting the partially hydrolyzed mixture obtained in step (b) with water having a temperature of about 80° to 100° C. to give a suspension with a liquid:solid ratio of about 5:1 and a sulfuric acid concentration of about 12%;

(d) agitating the diluted mixture obtained in step (c), e.g. for about 1 to 4 hours at about 80° to 100° C. to give a digested material;

(e) removing the insoluble component containing essentially all of the heavy metals from the soluble component obtained in step (d); and (f) processing the soluble component to produce ethanol.

Surprisingly, the aforementioned integrated processes allow for the highly efficient and cost effective production of ethanol from sewage sludge and/or municipal solid waste.

BRIEF DESCRIPTION OF THE FIGURE

The method of waste recovery including features of the invention is depicted in the attached schematic drawing, which forms a portion of this disclosure, wherein.

Figure 1:
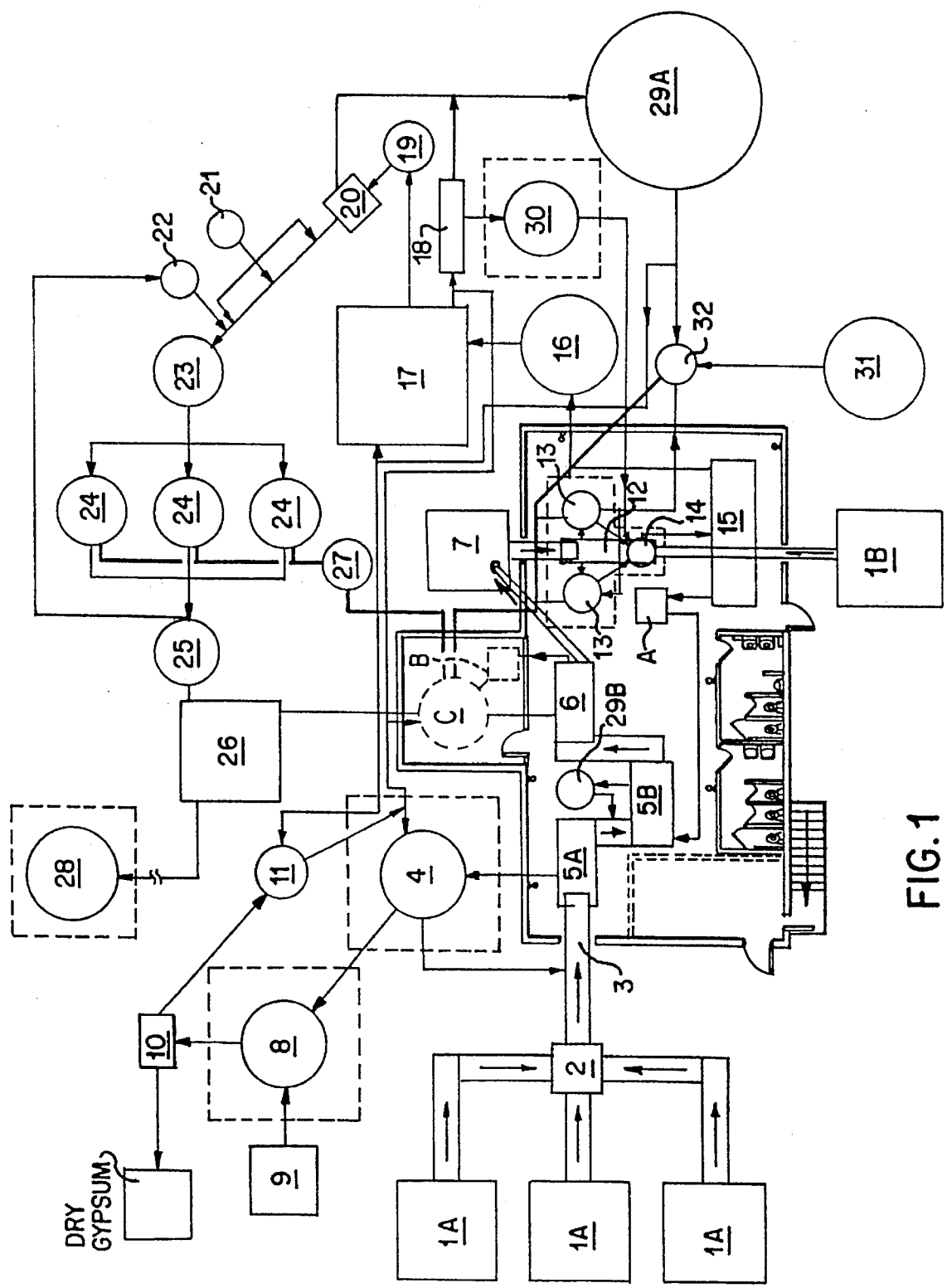
FIG. 1 is a flow chart detailing the complete process for the treatment of municipal solid waste material and/or sewage sludge.

| Reference | Equipment Description |
|---|---|
| 1A/1B | Raw Feedstock Storage Silo |
| 2 | Metering Vessel |
| 3 | Pre-Treatment Chamber |
| 4 | Dilute Sulfuric Acid Storage Vessel |
| 5A | Primary Screw Press |
| 5B | Secondary Screw Press |
| 6 | Dryer |
| 7 | Processed Feedstock Storage Vessel |
| 8 | Dilute Sulfuric Acid Neutralization Vessel |
| 9 | Lime Holding Vessel |
| 10 | Gypsum Belt Press |
| 11 | Neutralized Water Storage Vessel |
| 12 | Hydrolysis System |
| 13 | Cooking Vessels |
| 14 | Holding Vessel #1 |
| 15 | Filter Press |
| 16 | Acid Recovery Storage Vessel |
| 17 | Acid Recovery System |
| 18 | Evaporator |
| 19 | Holding Vessel #2 |
| 20 | Reverse Osmosis Filter |
| 21 | Ammonia and pH Balancing System |
| 22 | Yeast Injection System |
| 23 | Holding Vessel #3 |
| 24 | Fermentation Vessel |
| 25 | Yeast Filter and Distillation Holding Vessel |
| 26 | Distillation Column |
| 27 | Chillier Coil |
| 28 | Ethanol Storage Vessel |
| 29A/29B | Water Storage Vessel |
| 30 | Concentrated Sulfuric Acid Storage Vessel |
| 31 | Waste Water Storage Vessel (Optional) |
| 32 | Water Heater |
| A | Lignin Holding Vessel |
| B | Boiler Feedstock Storage Vessel |
| C | Boiler |

DESCRIPTION OF THE PREFERRED EMBODIMENTS

In the practice of the invention, the feed stock may be municipal solid waste material including waste obtained directly from a municipality or municipal solid waste that was previously land-filled and subsequently recovered. In addition to municipal solid waste, the feed stock can be sewage sludge, preferably in the form of sewage sludge cake which also contains substantial amounts of cellulosic material (about 35% weight:weight). The solid waste material is admitted into the facility through a fully automated receiving station. The waste material is then dumped onto a bulk conveyor. Any recyclable materials present such as valuable bulk items, ferrous metals, non-ferrous metals such as aluminum, glass, plastic, and rubber and the are then recovered. Methods for recovering such items are well known and disclosed, for example, in U.S. Pat. Nos. 5,184,780, 5,104,419, 5,060,871, 5,009,672, 4,974,781, 4,874,134, 4,692,167, 4,553,977, 4,541,530, 4,341,353, 4,069,145, and 4,063,903, the contents of each of which are fully incorporated by reference herein.

Preferably, the scrap tire materials are segregated onto a separate bulk conveyor which leads to a scrap tire processing and rubber recovery system, where the scrap tires are shredded and the rubber, steel and fiber are removed.

A remote controlled magnetic crane is used to remove any oversized, bulky ferrous materials from the solid waste conveyor. These oversized materials are then processed through a shredder which reduces the material to a workable size. The material is then sent to a recycling bin to await baling.

The waste material remaining after the oversized material is removed is then classified by the use of a trommel or other screening mechanism which disrupts any bags and yields two separate processing streams. By appropriate classification, one stream will contain organic waste composed primarily of cellulosic material, while the other will contain metallic products of a particular size, plastic, glass and rubber.

The waste materials are processed through several magnetic separations to remove any ferrous metals. The waste is then passed through an eddy current separator to remove any non-ferrous metals. The ferrous and non-ferrous metals are both conveyed to bins to await baling. The organic waste is then shredded and processed in the ethanol production system which accepts the waste material and processes it to obtain ethanol to be sold commercially.

Preferably, when sewage sludge is used it should first be dried to obtain a sewage sludge cake. Methods of dewatering sewage sludge to obtain sewage sludge cakes are well known in the art. For example, the moisture content of sewage sludge can be reduced by vacuum filters to 70–75%, to obtain a sewage sludge cake. Since sewage sludge cakes will normally not contain substantial amounts of recyclable materials (aluminum, glass, plastics, etc.), they can be directly treated with concentrated sulfuric acid and processed in the ethanol production system. However, if necessary, further drying of the sewage sludge cake can be achieved by flash or spray drying, where the sewage sludge cake particles are dried in suspension in a stream of hot gases to provide almost instantaneous removal of excess moisture. Rotary dryers and indirect heating systems can also be used. These drying techniques typically comprise a pug mill, rotary kiln dryer, dry cyclone and a web-scrubber. The aforementioned drying techniques are disclosed in Sludge Digestion and Disposal, *Public Works* 125 (5):D47-D58 (1994), the contents of which are fully incorporated by reference herein.

A portion of the byproducts from the ethanol process may be sold commercially and/or used to cogenerate electricity to aid in the operation of the facility. For example, the insoluble material obtained after hydrolysis of the cellulosic component of MSW and/or sewage sludge is primarily composed of lignin, a natural aromatic organic polymer found in all vascular plants. It has been surprisingly found that by using the lignin as a boiler fuel, the total energy costs for operating a processing facility as disclosed herein can be significantly decreased. Based upon the aforementioned energy savings, it has been unexpectedly discovered that the per gallon ethanol production cost can be reduced to about 15–20% below what it costs to produce ethanol from corn. Furthermore, the surprisingly high BTU per pound (about 4,000–13,350) rating of the obtained lignin can be increased by combining it with the clean burning, non-chlorinated plastic component of MSW. A technology capable of separating non-chlorinated plastic from chlorinated plastic (e.g. PVC), known as Vinyl Cycle™, is commercially available from National Recovery Technologies, Nashville, Tenn. The Vinyl Cycle™ technology is disclosed in U.S. Pat. No. 5,260,576, the contents of which are fully incorporated by reference herein. This composite lignin/plastic material can also be burned as a boiler fuel, thereby further decreasing the energy costs of the disclosed ethanol production process.

Any non-organic materials remaining after the aforementioned screening process may be pelletized and used commercially as additives for construction materials.

The present invention is entirely automated, requiring only routine maintenance at the end of each shift of operation. Fully automated screening techniques eliminate the need for unsanitary, hand sorting.

The present invention allows for a completely zero discharge facility. All buildings may be fully enclosed. All air and water pollutants may be captured and summarily treated. All materials entering the facility may be treated and converted into commercially workable materials.

These and other applications and advantages will become evident from the subsequent descriptions and design specifications.

Table I details the composition of dry municipal solid waste (MSW) as determined by the Environmental Protection Agency.

TABLE 1

| Composition of Municipal Solid Waste | |
|---|---|
| Organics | 74.0% |
| Ferrous Metals | 7.5% |
| Non-Ferrous Metals | 1.5% |
| Glass | 10.0% |
| Plastics | 5.0% |
| Non-Organics | 2.0% |

The present invention is designed to receive solid waste such as detailed in Table 1, municipal solid wastes that are recovered from land fills, and sewage sludge, preferably in the form of sewage sludge cake. The last two types of feed stocks will have a different composition than that depicted in Table 1, however this will not effect their use in the disclosed invention. The rate at which the solid waste may be processed through the system is greatly dependent on the size of the community that the present invention will serve. The system may handle from 25 tons per hour up to 125 tons or more per hour. The equipment may be sized accordingly.

The materials that are not treatable are hazardous waste, explosives and infectious wastes. The system is able to process refrigerators, washers, dryers, ranges, automobile scrap metal, large materials, small industrial waste and standard municipal solid waste. The present system is designed to recover plastics, glass, rubber, ferrous metals, and non-ferrous metals from the solid waste.

The trucks discharge the waste onto a bulk conveyor such as may be obtained from E&H Systems which traverses the length of the initial shredder building. A remote controlled magnetic crane is then used to remove any large metallic objects. These removed objects are placed into an automated pre-shredder for size reduction. Once the size reduction is completed, the waste is reintroduced into the system, into holding bins for baling on a standard baler.

A trommel screen as commonly available from such sources as MacLanahan Corporation is then used to automatically open bags, remove small impurities and crush any glass materials.

The material in the ethanol stream is conveyed through a series of five magnetic separators which will remove substantially all ferrous metals. That is to say, the waste stream which consists primarily of metallic and cellulosic components is delivered from the trommel to a series of inclined conveyors, each having a magnetic separator device, such as a drum or belt, as is well known in the art. The outlet end of each conveyor is supported at a height above the inlet of each succeeding conveyor such that the material passing the magnetic screen is subjected to gravitational agitation from one conveyor to the next, thereby enhancing magnetic recovery of remaining ferrous metals by a subsequent magnetic separator. The conveyor design is such that it will allow for the fully automated extraction of ferrous metals into a centralized area. This conveyor design also allows for the mixing of the materials to ensure 98% removal of all ferrous metals. The extracted ferrous metals fall down a vertical chute and are conveyed out of the facility to a holding bin for recycling.

The remaining material is then conveyed to an eddy current separator such as an Eriez Ferrous Metal Separator. The eddy current separator is utilized for the automated removal of the non-ferrous metal materials including batteries.

The eddy current separator is placed after the magnetic separators to ensure that no ferrous metals will damage the eddy current separator equipment. The presence of any ferrous metal materials in or on the eddy current separator will result in serious and expensive damage to the eddy current separator. The remaining waste materials are fed by the conveyor into a hammermill shredder which reduces the material to about a minus 3" to minus 4" size. The reduction in size of the material aids in the ethanol production process.

The hammermill shredder will include an explosion proof shroud to eliminate any potential dust related explosions.

The material flow may be divided into two distinct paths; the ethanol production process and a humus production path. The distribution of the waste between the two systems depends on the exact volume of waste coming into the facility.

As discussed previously, feed stock consisting of sewage sludge or sewage sludge cake will normally be able to bypass the above described sorting process and be directly treated with concentrated sulfuric acid for processing in the ethanol production system.

The process employed in the present invention is comprehensively outlined below with reference to FIG. 1.

Process Diagram Overview

The level of heavy metals found in the cellulosic component of sewage sludge (and cakes composed thereof) or MSW can vary significantly depending upon the source of the waste. For instance the hydrolyzate generated from the cellulosic component of MSW obtained from urban or highly industrialized areas can be contaminated with heavy metals to an extent that the subsequent yeast fermentation process can be inhibited. Therefore, these types of MSW samples may be treated to reduce their heavy metal content prior to hydrolyzation to avoid contaminating the fermentation liquor. On the other hand, it has been discovered that the removal of heavy metals from less contaminated samples can be accomplished via an efficient ion exchange process after the hydrolysis of the cellulosic feedstock.

The following discussion describes two processes which can be utilized to reduce the heavy metal content of the cellulose component of the feed stock. One which reduces the heavy metal content prior to hydrolyzation, and the other after hydrolyzation. Which process is used can be determined based upon the level of heavy metal contamination found in the feedstock.

A. A Process for the Automated Treatment of MSW
Stage 1: Pre-Treatment
Ref. 1A/1B–11
Purpose:
The purpose of the Pre-treatment Process is to separate the heavy metals that may inhibit fermentation of the hydrolyzed cellulosic component of MSW and/or sewage sludge by mixing the incoming shredded cellulosic component with dilute sulfuric acid. The solids are then pressed and the liquids are treated with lime, creating a byproduct, gypsum. The gypsum is then removed and the remaining solids are prepared to be broken down into sugars in the Hydrolysis System.

Based on data from many sources, which are summarized in "the Chemistry and Biology of Yeasts," A. H. Cook, ed., Academic Press, New York, pp. 296–303 (1958), some heavy metals are necessary for fermentation but at high concentrations can inhibit the fermentation of glucose and xylose by yeast. The approximate effects are shown in Table 2:

TABLE 2

Effects of Heavy Metals on Fermentation by Yeast

| Heavy Metal | Optimum Fermentation Concentration (ppm) | Concentration that Moderately Inhibits Fermentation (ppm) | Concentration that Severely Inhibits Fermentation (ppm) |
| --- | --- | --- | --- |
| Cadmium | 0 | 0.1 | 2 |
| Nickel | 0 | 40 | 100 |
| Lead | 0 | 0.3 | 10 |
| Chromium | 1 | 50 | 150 |
| Zinc | 5 | 200 | 400 |
| Copper | 7–8 | 15 | 30 |
| Iron | 10–30 | 500 | 1200 |

As previously discussed some feed stock will have levels of cadmium and iron which moderately inhibit yeast fermentation, and levels of lead, zinc and copper which severely inhibit yeast fermentation. Thus, the reduction of heavy metals found in this type of feedstock is critical to achieve the efficient fermentation of the obtained sugars. A sample treated according to the pretreatment process which has substantially no trace metals is one which has at least about a 70% reduction of these metals.

Description:

Raw Feedstock Silos (Ref. 1A and 1B) receive feedstock of about 85%–90% pure organic material in a pre-shredded state of –2" (⅝"×2") particulate size. Each Silo holds about 25 tons of material, roughly equivalent to a 2½ days supply of feedstock. Materials having no detectable heavy metal content do not require pre-treatment so they are stored separately in Silo 1B.

Material is conveyed from Silo 1A by bulk conveyor to a Metering Silo (Ref. 2). The Metering Silo dispenses the untreated feedstock to a Pre-Treatment Chamber (Ref. 3) while dilute sulfuric acid (about 1 to 10% by weight) is mixed with the feedstock at about 40° to 100° C. This allows for the dissolution of heavy metals and chlorides (metal chlorides and possibly organic chlorides) from the feedstock. The material is then conveyed by a screw conveyor to Screw Presses (Ref. 5A and 5B) enabling the removal of about 60%–80% of the liquid content, thereby removing the soluble component from the insoluble component. A secondary wash is required to eliminate any trace acid (Ref. 5B). The solids from the Screw Press are then fed into a Conveyor Dryer (Ref. 6) with a feed rate of about 3.25 tons per hour. The Conveyor Dryer further reduces the moisture content of the feedstock to about 5%–10%. The dried insoluble component, having a light, fluffy consistency, is pneumatically conveyed to a Feed Process Storage Silo (Ref. 7).

The liquids from the Screw Press are piped back into the Dilute Sulfuric Acid Storage Vessel (Ref. 4) for reuse. In addition, dilute acid from the Acid Recover), System (Ref. 17) is piped to the Dilute Acid Storage Vessel. Heavy metals and sediment from the Storage Vessel are evacuated to a Neutralization Tank (Ref. 8). The liquid in the Neutralization Tank is mixed with lime and pumped to a Belt Press (Ref. 10) where gypsum is removed. The remaining neutralized fluid, consisting of $H_2O$ and particulate, is then run through a particulate filter and returned to a Water Holding Vessel (Ref. 11) for reuse in the system.

As discussed below, an alternative ion exchange process for removing essentially the heavy metals involves carrying out the hydrolyzation step outlined below and recovering the aqueous-insoluble lignin. It has been discovered that essentially all of the heavy metals are bound to the lignin.

Stage 2: Hydrolyzation

Ref. 12–16, 31, A, B, C

Purpose:

The purpose of the Hydrolyzation Process is to break down the molecular structure of the feedstock into sugars by mixing the material with concentrated (about 65 to 93%, preferably, about 70%) sulfuric acid. The sugar/acid/water solution is cooked for a determined period of time after which the solids are removed. The solution is sent to the Acid Recovery System for separation.

Description:

Pre-treated feedstock is metered from the Storage Silo (Ref. 7 or Ref. 1B) to the Hydrolysis System (Ref. 12) where about 70% concentrated sulfuric acid is automatically introduced at about a 1:1 ratio. Unless otherwise indicated, all ratios and % content recited herein are based upon a weight-:weight ratio. Where recited, a ratio of about 1:1 includes compositions comprised of a 60:40 to 40:60 by weight mixture. Preferably, the ratio of concentrated sulfuric acid to pre-treated feed stock is about 45:55 to 55:45 by weight.

Material is blended for about 2 to 15 minutes, preferably about 10 minutes, and fed into Cooking Vessels (Ref. 13) along with water raised to the temperature of about 88° C. This solution consists of about a 2:1 ratio (about 2 parts water to about 1 part hydrolyzed material by weight). This material is agitated slowly, while maintaining a constant temperature of about 96° C. for about 1–4 hours. Under these conditions, the cellulose and hemicellulose are converted to glucose and xylose, respectively. At the end of this period, the Cooking Vessels are evacuated into a Holding Vessel (Ref. 14) to allow the Cooking Vessel to be recharged. The Holding Vessel stabilizes the temperature of the material and regulates the flow to the Filter Press (Ref. 15).

Material from the Holding Vessel is then filtered for example by pumping it into a Filter Press (Ref. 15) which removes the suspended solids to give a filtrate. The solids may be pulverized, washed and returned to the Dryer (Ref. 6) for use as boiler fuel. The filtrate is then pumped from the Filter Press to the Acid Recovery Storage Vessel (Ref. 16).

Note: Municipal waste water from the Waste Water Storage Vessel (Ref. 31) may be used as a substitute for fresh water in the Hydrolysis System (Ref. 12). All pathogens inherent in the waste water are eliminated in the Hydrolysis System. The high nitrogen content of the waste water is retained, virtually eliminating the need for the addition of ammonia (a yeast nutrient useful in the fermentation process).

Stage 3. Acid Recovery

Ref. 16–19

Purpose:

The purpose of the Acid Recovery Process is to recover the sulfuric acid from the sugar/acid/water solution to give an acid-containing solution and a sugar-containing solution. The concentrated sulfuric acid and water are then reused in the system. Once the sugars and water have been removed from the solution it is piped into the Fermentation Tanks to be fermented into ethanol.

There are a number of well known methods for recovering sulfuric acid from an aqueous stream, any one of which may be used in the practice of the invention. For example, the aqueous stream may be passed through an activated charcoal filter to retain the sugars, and washed with water to rinse the remaining acid. The adsorbed sugar may then be eluted by washing with heated alcohol. See, M. R. Moore and J. W. Barrier, "Ethanol from Cellulosic Residues and Crops," Annual Report, DOE/SERI Contract No. DK-6-06103-1, Tennessee Valley Authority, Muscle Shoals, Ala., October 1987, pp. 27–49, the contents of which are incorporated by reference herein. However, this method for separating the sulfuric acid from the sugars is not preferred, as the alcohol must be evaporated from the resulting sugar solution before fermentation, which adds another step requiring energy input. Problems may also be encountered with acid carry-over between the adsorption and desorption cycles which can be ameliorated by use of a nitrogen surge between the cycles. Problems may also be encountered with the effluent alcohol (ethanol) not being saturated at 70° C., resulting in a lower sugar capacity. Lower ethanol flow rates and increased desorption cycle times enhance the desorption of the sugars to give effluent streams which are 95–100% saturated with sugar.

More preferably, ion exchange resins may be used to separate the acid and sugar into an acid containing stream and a sugar containing stream. Such resins include the Amberlite strongly acidic cation exchanger resins of the "GEL" type, e.g. IR 120 PLUS sulfuric acid functionality, which is commercially available from the Aldrich Chemical Company. The sugar is adsorbed on the strongly acidic resin giving an acid containing stream which can be recycled. The adsorbed sugars are then recovered by eluting the resin with pure water. See, M. R. Moore and J. W. Barrier, "Ethanol from Cellulosic Residues and Crops," Annual Report, DOE/SERI Contract No. DK-6-06103-1, Tennessee Valley Authority, Muscle Shoals, Ala., October 1987, pp. 30–39, the contents of which are incorporated by reference herein. An apparatus which allows for the continuous separation of acid and sugar containing streams is commercially available from Advanced Separation Technologies Incorporated, Lakeland, Fla. (Model ISEP LC2000), which employs a strongly acidic ion-exchange resin (Finex CS16G, 310 micron mean size). Such apparatuses are disclosed, for example, in U.S. Pat. Nos. 4,522,726 and 4,764,276, the contents of which are fully incorporated by reference herein.

It is also possible to separate the acid and the sugar using a solvent, which selectively extracts and removes the acid from the aqueous solution of the sugar. See, M. R. Moore and J. W. Barrier, "Ethanol from Cellulosic Residues and Crops," Annual Report, DOE/SERI Contract No. DK-6-06103-1, Tennessee Valley Authority, Muscle Shoals, Ala., October 1987, pp. 39–49, the contents of which are incorporated by reference herein. The separation may be carried out on a Karr reciprocating-plate extraction column. The column has receiving vessels at each end for solvent and hydrolyzate separation. Mixing is accomplished by teflon plates coupled to a motor. The acid-sugar solution is added to the top of the column which travels down the column where the aqueous solution is intimately admixed with the solvent. The solvent is added to the bottom of the column. An aqueous solution containing the sugar is drawn off the bottom of the column while the acid containing solvent solution is drawn off the top. The acid may then be recovered from the solvent, for example, by distillation of the solvent or by washing the solvent with distilled water. An apparatus and solvent for the continuous separation of acid from aqueous sugar solutions is available, for example, from Glitsch, Inc., Parsippany, N.J.

It is expected that the sugar stream obtained from any of these separation processes will contain residual acid. Preferably, the residual acid is then neutralized with lime or ammonia to a pH of about 6.

Description:

Liquid containing about 10% sugar, 10% acid, and 80% water is pumped from the Acid Recovery Storage Vessel (Ref. 16) to the Acid Recovery System (Ref. 17) which separates the liquid into an acid/water solution and a sugar/water solution. The sugar/water solution is pumped to a Holding Vessel (Ref. 19); the recovered acid/water solution is pumped to an Evaporator (Ref. 18) where water is removed from the acid by evaporated and returned to the Water Storage Vessel (Ref. 29A). Removing the water brings the acid concentration to its original level of about 70%. This allows for the return of the acid from the Evaporator to the Concentrated Acid Storage Vessel (Ref. 30) for reuse into the system.

Stage 4: Fermentation
Ref. 19–24
Purpose:

The purpose of the Fermentation Process is to concentrate the sugar solution and blend it with yeast for the production of an ethanol/water solution. The sugar solution may be concentrated to about 12–14% by evaporation (e.g., by application of heat and/or a vacuum) or with a reverse osmosis filter.

After fermentation, the ethanol is recovered. The yeast may or may not be removed prior to recovery of the ethanol. As discussed below, the ethanol may be recovered by distillation or, in the alternative, may be recovered by solvent extraction with a solvent which is non-toxic to the fermentation microorganisms. See, U.S. Pat. No. 5,036,005, the contents of which are fully incorporated by reference herein. The yeast may also be removed by centrifugation. See, U.S. Pat. No. 4,952,503, the contents of which are fully incorporated by reference herein. Preferably, the remaining yeast is first removed and the fermented liquid is pumped to the Distillation Column for the extraction of ethanol.

Methods for fermenting hexoses and pentoses obtained from hydrolyzed cellulosic materials and recovering the ethanol are well known and taught, for example, in U.S. Pat. Nos. 5,198,074, 5,135,861, 5,036,005, 4,952,503, 4,650,689, 4,384,897, 4,288,550, the contents of which are fully incorporated by reference herein.

Description:

From the Holding Vessel (Ref. 19), sugar, water and trace acid (less than about 0.1%) are pumped through the Reverse Osmosis Filter (Ref. 20) to remove some of the water in solution and bring the sugar concentration to around 12%–14%. Ammonia is added and the pH carefully monitored to ensure the required pH balance of about 6 for optimal fermentation. At this point, yeast is added (Ref. 22), blended and pumped into a Holding Vessel (Ref. 23) and subsequently into Fermentation Tanks (Ref. 24). The mixture is held for about 48 hours. A Chillier Coil (Ref. 27) helps maintain the required temperature of about 36° C. for fermentation. After 48 hours, the fermented liquid is metered to a filter and holding vessel (Ref. 25) where the yeast is removed and piped to the Yeast Storage Vessel. The remaining liquid is metered to a Holding Vessel (Ref. 25) and subsequently to the Distillation Column (Ref. 26).

Stage 5. Ethanol Recovery Process

Ref. 25–26

Purpose:

The purpose of the ethanol recovery is to separate the ethanol from the ethanol/water solution by means of evaporation and condensation. This results in the production of pure ethanol as well as the by-product stillage.

Description:

Fermented stock is metered to the Distillation Column (Ref. 26). Depending on the original feedstock, the yield may range from 60 to 120 gallons of 180–190 proof ethanol per ton of input material. The ethanol from the Distillation Column is pumped to the Ethanol Storage Vessel (Ref. 28). The Ethanol Storage Vessel (Ref. 28) will have a storage capacity of 12,000 gallons of ethanol, roughly equivalent to a 12 to 14 day supply of ethanol manufactured in the process.

A by-product of the distillation process is stillage. Stillage is a starchy residue that can be sold as cattle feed, or further processed to produce other valuable substances and/or chemicals.

B. An Ion Exchange Process for the Removal of Heavy Metals from MSW

It has been surprisingly discovered that the level of heavy metal contamination typically found in MSW or sewage sludge is low enough so the associated heavy metals essentially remain coordinated with the insoluble fraction obtained after acid hydrolysis of the cellulosic component. Therefore concentrations of soluble heavy metals remaining in the hydrolyzate are well below levels which interfere with fermentation. Based upon this discovery, the present invention further relates to an efficient process for the post-hydrolysis removal of heavy metals from the cellulosic component of MSW and/or sewage sludge.

The steps for processing the feedstock are similar to the ones described herein above with the exception that the removal of the heavy metals from the pre-shredded feed stock is delayed until after the hydrolysis step. By doing so, the step involving the pretreatment of the cellulosic material with dilute sulfuric acid can be eliminated, thereby eliminating the need for a secondary wash and the time-consuming, energy-intensive, step of drying the pretreated feedstock. Therefore, rather than pretreating the preshred feedstock with dilute sulfuric acid, it is directly fed into the hydrolysis system where about 70% concentrated sulfuric acid is automatically introduced at about a 1:1 (acid/sample) ratio. This suspension is then blended at around 30°–80° C. for preferably about 2–20 minutes, or more preferably about 2–15 minutes, then fed into cooking vessels where the suspension is diluted with water having a temperature of about 80° to 100° C. until the liquid-to-solid ratio 5:1 and the sulfuric acid concentration is about 12%. This material is agitated while maintaining a constant temperature of about 80°–100° C. for about 1–4 hours. Under these conditions the conversion of cellulose and hemicellulose to glucose and xylose is 87–100% complete.

Once the hydrolysis is complete, the cooking vessels are evacuated into a holding vessel, thereby allowing the cooking vessel to be recharged. The holding vessels stabilize the temperature of the hydrolyzate and regulates its flow to the filter press where suspended solids are removed to give a filtrate. The filtrate is separated into an acid containing solution and a sugar containing solution and the sugar containing solution processed to produce ethanol.

The insoluble component collected from the filter press is dried, optionally mixed with the non-chlorinated plastic component of MSW, and utilized as a boiler fuel to produce energy, e.g., to cogenerate electricity, which can be sold or used in the operation of the processing facility, such as in the distillation process. If required, the level of heavy metals associated with the insoluble component can be reduced prior to burning by treatment with a 1–10% salt solution followed by a rinse with water.

Having now generally described this invention, the same will be understood by reference to the following examples which are provided herein for purposes of illustration only and is not intending to be limited unless otherwise specified. The entire text of all applications, patents and publications cited above and below are hereby incorporated by reference in their entirety.

EXAMPLES

Example 1

Removal of Heavy Metals from MSW by Pretreatment With Dilute Sulfuric Acid

A sample of municipal solid waste (including all solids) was analyzed for heavy metal content. The results were as follows (Table 3):

TABLE 3

| Metal | mg/kg (ppm) |
|---|---|
| Zinc | 86 |
| Copper | 30 |
| Chromium | 10.6 |
| Cadmium | 0.6 |
| Lead | 20 |
| Iron | 1190 |
| Nickel | 0.5 |
| Tin | >1 (not detected) |

A 20 gm sample of MSW in 200 g of 2% aqueous sulfuric acid was heated to reflux for 2 hours. The solids were filtered, washed, and submitted for analysis (Table 4):

TABLE 4

| Metal | mg/kg (ppm) | % Reduction |
|---|---|---|
| Zinc | 7.8 | 91 |
| Copper | 3.0 | 90 |
| Chromium | 2.4 | 77 |
| Cadmium | N.D.[1] | 100 |
| Lead | 6.0 | 70 |
| Iron | 98 | 92 |
| Nickel | N.D. | 100 |
| Tin | N.D. | — |

[1]N.D. = Not detected.

These data show that a simple dilute, hot acid wash effectively reduces the levels of heavy metals in MSW, which can inhibit the production of ethanol by fermentation.

Example 2

Removal of Heavy Metals from MSW via an Ion Exchange Process

MSW samples were mixed together to form a composite sample. Four samples were then taken from the composite sample and analyzed for cellulose, lignin, and ash using the following procedure.

The composite MSW samples were dried to less than 1% moisture in a microwave oven, and then ground to pass a 20 mesh screen. The samples were then mixed with an equal amount (weight) of 10% sulfuric acid and heated for two hours at about 100° C. After heating the solids were collected, dried, and weighted. The weight loss resulting from the treatment with 10% sulfuric acid represents the hemicellulose content of the MSW sample. The collected solids were then mixed with 70% sulfuric acid and placed in a reactor containing 5 parts water to 1 part solids and heated at about 100° C. for 3 hours in a microwave oven. The solids were then filtered from the slurry and the glucose content determined. The filtered solids were then dried, heated at about 600° C., and the ash content determined. The lignin content of each sample was determined by the difference in the weight of ash contained in the sample and the total weight of the sample.

The results, presented in Table 5, show that the composite sample was homogeneous with respect to cellulose, lignin, ash, and hemicellulose.

TABLE 5

| Test No. | Cellulose, % | Lignin, % | Ash, % | Hemicellulose, % |
|---|---|---|---|---|
| 1 | 53 | 20 | 18 | 9 |
| 2 | 55 | 20 | 18 | 7 |
| 3 | 58 | 18 | 17 | 7 |
| 4 | 56 | 19 | 19 | 6 |
| Average | 55 | 19 | 18 | 7 |

A 100 g sample of the MSW and 100 g (acid:sample ratio 1:1) of 70% sulfuric acid were completely mixed until a black paste was formed. The temperature was maintained at about 30° C. during the 20 minute mixing time. The reaction mixture was then added to water preheated to about 88° C. to give a 5:1 water to solids ratio and a sulfuric acid concentration of about 12%. The slurry was then heated at about 100° C. for about 2–3 hours to complete the hydrolysis process. Once completed, the hydrolyzate liquid and the residual solids were separated and analyzed for carbohydrate and heavy metal content.

Analysis of Hydrolysis Residual Solids

The residual solids obtained from the hydrolysis process were analyzed for cellulose, lignin, and ash content using the previously described procedure. The results are presented in Table 6.

TABLE 6

| Cellulose, % | Lignin, % | Ash, % |
|---|---|---|
| 7 | 49 | 44 |

These results clearly demonstrate that the hydrolysis conditions of the present invention are sufficient to significantly reduce the cellulose content of cellulosic MSW and/or sewage sludge.

Analysis of Hydrolyzate Liquid

The hydrolyzate liquid was neutralized with a known volume of sodium hydroxide. The neutralized sample was then analyzed for glucose content using a YSI model 20 glucose analyzer. The results of this procedure reveal that the hydrolyzate contained about 10% sugar (corrected for dilution). The theoretical yield of sugar is 10.4%. Error in analysis and decomposition of some of the glucose most likely accounts for the difference.

Analysis of the Hydrolyzate and the Insoluble Component for Heavy Metals

The original composite MSW sample, the hydrolyzate residual solids, and the hydrolyzate liquid (the heavy metal content of the hydrolyzate is based on dry weight) were analyzed to determine levels of copper, zinc, chromium, nickel, and iron. These heavy metals were found in previously analyzed prehydrolysis MSW samples at levels which may hinder fermentation. The results of this analysis are presented in Table 7.

TABLE 7

| Metal | MSW (ppm)[1] | Hydrolyzate (ppm)[1] | Insoluble component from Hydrolyzate (ppm)[1] |
|---|---|---|---|
| Copper | 18 | 0.94 | 50 |
| Zinc | 140 | 23 | 39 |
| Nickel | 10 | 2.1 | 7.1 |
| Iron | 2,300 | 480 | 1,100 |
| Chromium | 12 | 4.0 | 17 |

[1]Based upon dry weight.

The original prehydrolysis MSW feedstock contained about the expected levels of heavy metals. However, surprisingly, the insoluble residue obtained after the hydrolysis step contained much higher concentrations of heavy metals than expected based upon the pretreatment studies. While the inventors do not wish to be bound by any particular theory, it appears that the residual solids may have been partially oxidized during the hydrolysis reaction converting them into low-grade ion-exchange resins which bind the heavy metals. The residue retained over 90% of the copper, 55% of the chromium, and 20–30% of the zinc, nickel, and iron. The two heavy metals that interfere most with fermentation are copper and chromium. As a result of the heavy metals remaining with the insoluble residue, the concentration of heavy metals in the hydrolyzate is, in most cases, well below levels which interfere with fermentation. Moreover, it is expected that most of the heavy metals in the hydrolyzate will go with the acid stream during acid/sugar separation, further reducing the heavy metal content. A sample treated according to the present ion-exchange process which has essentially all of the heavy metals removed from the hydrolyzate is one which has about 90% of the copper, about 55% of the chromium, and about 20–30% of the zinc, nickel, and iron retained in the insoluble component.

Example 3

The Effect of Heavy Metals on Hydrolysis and Fermentation

The following procedure was used to determine whether the buildup of Cu, Zn, Cr, Ni, and Fe in the recycled acid would affect hydrolysis of cellulosic MSW and/or sewage sludge. Cotton lint, a cellulosic material which does not contain any heavy metals, was hydrolyzed using the procedure described herein above with the exception that the sulfate salts of Cu, Zn, Cr, Ni, and Fe were added to the 70% acid at concentrations 20 times that expected based upon the data presented in Table 7. The conversion of cellulose to glucose was measured and compared to the conversion obtained without the addition of the heavy metals (controls). Duplicate reactions were run and the percent conversion of cellulose to glucose for samples containing the heavy metals was 85% and 87% as compared to 86% and 87% for controls. The results from these experiments demonstrate that concentrations of these heavy metals up to 20 times the levels expected in the MSW hydrolyzate liquid do not significantly effect hydrolysis.

Effect of heavy metals on the fermentation of pure glucose was also tested using the following procedure. Two 5% glucose solutions containing the appropriate nutrients (e.g. ammonium sulfate) were prepared and the pH adjusted to 5.5. The solutions were then fermented with common yeast for 72 hours and the remaining glucose measured. Based upon the glucose remaining in solution after fermentation, about 94%–96% of the glucose was consumed by the yeast during the fermentation period.

The fermentation experiment was repeated with the exception that the sulfate salts of the heavy metals normally found in MSW were added at 10 and 20 times the concentrations shown for the hydrolyzate in Table 7. Under these conditions the amount of glucose consumed was 92%–93% and 61%–65% for the fermentation solution containing 10 and 20 times the heavy metal concentrations shown for the hydrolyzate in Table 7, respectively.

Similar to the effect on hydrolysis, the results obtained with the fermentation experiment show that heavy metal concentrations up to 10 times those expected in the MSW hydrolyzate do not significantly effect the rate or extent of glucose fermentation. Moreover, the fermentation rate was not decreased until heavy metal levels reached 20 times the concentration expected in the MSW hydrolyzate.

Based upon these results, it is clear that the pretreatment step to remove heavy metals from MSW or sewage sludge is not always necessary to prevent problems with fermentation or hydrolysis since the heavy metals normally found in the feedstock, to a large extent, may be removed with the solid residue produced during the hydrolysis step. Because the heavy metals are associated with the solid residue, their levels in the liquid hydrolyzate product are well below the concentrations that adversely affect the hydrolysis reaction and the fermentation step. However, for MSW and/or sewage sludge samples having a high level of heavy metal contamination, it may be necessary to pretreat the cellulosic feedstock or hydrolyzate prior to fermentation as described herein.

Example 4

Removal of Heavy Metals from the Hydrolyzate Prior to Fermentation

As previously demonstrated, the presence of excessive amounts of heavy metals in the hydrolyzate will interfere with glucose fermentation. Therefore, in the unusual instance where excessive heavy metals are detected in the hydrolyzate the following procedure can be used for their removal.

Lime was added to the hydrolyzate until a pH of about 10.5–11 was reached. The gypsum and excess lime were then filtered from the slurry and the heavy metal concentration of the hydrolyzate measured. The heavy metals in the hydrolyzate were reduced according to the results presented in Table 8.

TABLE 8

| Metal | Initial ppm | Final ppm | % Change |
| --- | --- | --- | --- |
| Copper | 0.94 | 0.19 | 80 |
| Nickel | 2.1 | 1.5 | 29 |
| Chromium | 4 | 0.4 | 90 |
| Iron | 480 | 66 | 86 |

The heavy metal concentrations in the test hydrolyzate after the addition of lime are too low to severely inhibit the fermentation process. It should also be noted that the heavy metals that most affect fermentation, copper and chromium, are 80%–90% removed by the addition of lime. Therefore, if a hydrolyzate is obtained which has a concentration of heavy metals great enough to severely inhibit fermentation, the addition of lime will alleviate this problem.

Example 5

Removal of Heavy Metals from the Residue Obtained after Hydrolysis

If required, the level of heavy metals associated with the insoluble component obtained after hydrolysis can be reduced prior to burning by the following procedure. The insoluble component was collected and washed with a 1% NaCl solution at room temperature. Once washed, the insoluble component was separated from the NaCl solution and amount of associated heavy metals measured. The heavy metals associated with the insoluble component were reduced according to the results presented in Table 9.

TABLE 9

| Metal | Initial ppm | Final ppm | % Change |
| --- | --- | --- | --- |
| Copper | 50 | 13 | 74 |
| Nickel | 7.1 | 2.9 | 59 |
| Chromium | 17 | 5.3 | 69 |
| Iron | 1100 | 260 | 76 |

These results demonstrate that the level of heavy metals associated with the insoluble component obtained after hydrolysis can be reduced with a salt wash prior to burning as a fuel.

Example 6

Separation of Sugars from Surfuric Acid

In the following example, ISEP LC200 employing the resin Finex CS16G, 310 micron mean size, obtained from Advanced Separation Technologies Incorporated, Lakeland Fla., was used to separate the sugars from sulfuric acid of a 4.5% sugar/4.2% acid (wt.) solution.

The resin volume was 1.22 ft$^3$. The feed of sugar/acid solution was 0.082 BV (bed volumes)/hr. The resin was washed with 1.65 gal water/gal of feed. The results were as follows:

TABLE 10

|  | Sugar Product | Acid Product |
| --- | --- | --- |
| Recovery | 99.87% | 96.08% |
| Purity | 95.5% | 99.88% |
| Concentration | 4.0% | 4.25% |

Thus, the ISEP equipment is able to efficiently separate the sugars from the sulfuric acid, allowing the sulfuric acid to be recycled in the process.

Example 7

Analysis of the Lignin and Gypsum Materials Produced by the Hydrolysis Process

In order to determine the physical and chemical characteristics of the lignin and gypsum materials produced by the disclosed hydrolysis processes, typical MSW samples were sorted, shredded, and hydrolyzed according to the present invention. The obtained lignin was analyzed following EPA and ASTM testing standards to determine its pre- and post-ignition physical and chemical characteristics. Where indicated, the lignin was analyzed according to the Toxicity Characteristic Leaching Procedure (TCLP) which involves an 18-hour extraction of a sample with either an acetic acid or sodium acetate solution and the subsequent analysis of the leachate for contaminates including metals, pesticides, and semi-volatile organic compounds. The details of TCLP are set forth in Test Methods for Evaluating Solid Waste, Physical/Chemical Methods, EPA Publication SW-846, the contents of which are fully incorporated by reference herein. The results of this analysis are presented in Table 11.

TABLE 11

| Test | Result[1] |
|---|---|
| General | |
| pH of TCLP Extract[2] | 4.91 |
| pH of TCLP Extract Fluid | 1 |
| Metals | |
| Arsenic, TCLP Extractable | 0.11 mg/l |
| Barium, TCLP Extractable | 1.35 mg/l |
| Cadmium, TCLP Extractable | 0.05 mg/l |
| Chromium | 2.2 ppm |
| Chromium, TCLP Extractable | 0.13 mg/l |
| Copper | 58 ppm |
| Lead | 11 ppm |
| Lead, TCLP Extractable | 0.11 mg/l |
| Mercury, TCLP Extractable | 0.0002 mg/l |
| Nickel | <0.7 ppm |
| Selenium, TCLP Extractable | 0.07 mg/l |
| Silver, TCLP Extractable | 0.05 mg/l |
| Zinc | 2.4 ppm |
| Volatiles | |
| Benzene, TCLP Extractable | 0.001 mg/l |
| Carbon Tetrachloride, TCLP Extractable | 0.001 mg/l |
| Chlorobenzene, TCLP Extractable | 0.001 mg/l |
| Chloroform, TCLP Extractable | 0.001 mg/l |
| 1,4-Dichlorobenzene, TCLP Extractable | 0.001 mg/l |
| 1,2-Dichlorobenzene, TCLP Extractable | 0.001 mg/l |
| 1,1-Dichloroethylene, TCLP Extractable | 0.001 mg/l |
| Methyl Ethyl Ketone, TCLP Extractable | 0.003 mg/l |
| Tetrachloroethylene, TCLP Extractable | 0.001 mg/l |
| Trichloroethylene, TCLP Extractable | 0.001 mg/l |
| Vinyl Chloride, TCLP Extractable | 0.001 mg/l |
| Non-Volatiles | |
| o-Cresol, TCLP Extractable | 0.05 mg/l |
| m,p-Cresol, TCLP Extractable | 0.10 mg/l |
| 2,4-Dinitrotoluene, TCLP Extractable | 0.05 mg/l |
| Hexachlorobenzene, TCLP Extractable | 0.05 mg/l |
| Hexachlorobutadiene, TCLP Extractable | 0.05 mg/l |
| Hexachloroethane, TCLP Extractable | 0.05 mg/l |
| Nitrobenzene, TCLP Extractable | 0.05 mg/l |
| Pentachlorophenol, TCLP Extractable | 0.05 mg/l |
| Pyridine, TCLP Extractable | 0.10 mg/l |
| 2,4,5-Trichlorophenol, TCLP Extractable | 0.05 mg/l |
| 2,4,6-Trichlorophenol, TCLP Extractable | 0.03 mg/l |
| Pesticides | |
| Chlordane, TCLP Extractable | 0.001 mg/l |
| Endrin, TCLP Extractable | 0.0002 mg/l |
| Heptachlor, TCLP Extractable | 0.0002 mg/l |
| Heptachlor epoxide, TCLP Extractable | 0.0001 mg/l |
| Lindane, TCLP Extractable | 0.0001 mg/l |
| Methoxychlor, TCLP Extractable | 0.0003 mg/l |
| Toxaphene, TCLP Extractable | 0.00005 mg/l |
| Herbicides | |
| 2,4-D, TCLP Extractable | 0.010 mg/l |
| 2,4,5-TP (Silvex), TCLP Extractable | 0.010 mg/l |
| Miscellaneous | |
| Solids Content of Sample | 100.00% |
| PCB, Total | 1 ppm |
| Dry Basis Data | |
| Ash, Dry | 20.86% |
| Heat of Combustion, Dry | 10564 BTU/lb |
| Carbon, Fixed, Dry | 18.91% |
| Volatiles, Dry | 60.23% |

TABLE 11-continued

| Test | Result[1] |
|---|---|
| Sulfur, Dry | 0.66% |
| As Received Basis | |
| Moisture, Total | 64.19% |
| Ash, As Received | 7.47% |
| Heat of Combustion, As Received | 37835 BTU/lb |
| Carbon, As Received | 6.77% |
| Volatiles, As Received | 21.57% |
| Sulfur, As Received | 0.24% |
| Ignited Basis, Elemental Form | |
| Aluminum, Ignited Basis | 17.10% |
| Calcium, Ignited Basis | 1.64% |
| Iron, Ignited Basis | 1.03% |
| Magnesium, Ignited Basis | 0.90% |
| Manganese, Ignited Basis | 0.03% |
| Potassium, Ignited Basis | 0.56% |
| Silica, Ignited Basis | 24.06% |
| Sodium, Ignited Basis | 1.62% |
| Sulfur, Ignited Basis | 0.10% |
| Titanium, Ignited Basis | 3.57% |
| Ignited Basis, Oxide Form | |
| Aluminum Oxide ($Al_2O_3$), Ignited Basis | 32.32% |
| Calcium Oxide (CaO), Ignited Basis | 2.30% |
| Iron Oxide ($Fe_2O_3$), Ignited Basis | 1.47% |
| Magnesium Oxide (MgO), Ignited Basis | 1.49% |
| Manganese Oxide ($MnO_2$), Ignited Basis | 0.04% |
| Potassium Oxide ($K_2O$), Ignited Basis | 0.67% |
| Silica Oxide ($SiO_2$), Ignited Basis | 51.49% |
| Sodium Oxide ($Na_2O$), Ignited Basis | 2.19% |
| Sulfur Trioxide ($SO_3$), Ignited Basis | 0.25% |
| Titanium Oxide ($TiO_2$), Ignited Basis | 5.96% |
| Sum of Ignited Basis Oxides | 98.18% |
| General | |
| Lignin and Tannins (water soluble) | 0.13% |
| Heat of Combustion, Moisture Ash Free | 13348 BTU/lb |

[1]Percentages are % by weight.

The results presented in Table 11 demonstrate that the lignin obtained by the disclosed hydrolysis procedures has acceptable levels of impurities and a surprisingly high BTU/lb rating. Therefore, the lignin obtained from processing the cellulosic component of MSW and/or sewage sludge according to the present invention represents a valuable fuel resource.

The gypsum produced was also analyzed according to EPA and ASTM standards. The results of this analysis are presented in Table 12 and show that the gypsum generated by the disclosed processes is suitable for use as a construction additive or other appropriate purposes.

TABLE 12

| Determinations | [1]Percent |
|---|---|
| Moisture | 10.2 |
| Ash | 83.9 |
| Sulfur | 16.9 |
| Metals | ppm |
| Lead | 38 |
| Copper | 9.5 |
| Nickel | 21 |
| Chromium | 40 |
| Zinc | 82 |

[1]Percent by weight.

Example 8

Production of Ethanol From MSW

The overall process of the present invention is set out in more detail in the following example.

Raw Feedstock Storage Silos (Ref. 1A/1B)

Description:
These stations will receive feedstock composed of 85%–90% pure organic material. Materials that may be used as feedstock include processed cottonseed waste, switch grass, paper pulp, textile bag house residue, agricultural waste, sugar beet waste, sugar cane waste, the cellulosic component of municipal solid waste (MSW) and sewage sludge, and any other similar feedstocks having the desired organic content. The cellulosic component of MSW or any other feedstock composed of large particles will be shredded to −2" or (⅝"×2") particulate size. Depending on the feedstock, each silo will store about 25 tons of material, which equals a two and one half (2½) days supply. Material that must be processed in the pre-treatment dilute sulfuric acid process will be stored in Ref: 1A silos: material not requiring pre-treatment will be stored in Ref: 1B silos.

Input:
Replenished as required. The Ethanol Production System is designed to process 10 tons per day of feedstock. While the silos will receive material in a batch process, on average, the rate of delivery will be 41.7 lbs/min (8 hours/day, 5 days/week).

Output:
Material to Metering Vessel: 41.7 lbs/min (8 hours/day, 5 days/week).

Specifications:
Raw Feedstock Storage Silos are constructed of 10' high modules. The modules are constructed of 12 gauge sheet welded steel and will be bolted together for various volume requirements.

Each silo has an approximate 2½ day storage area (using 15 lbs/ft$^3$ as a standard). Storage capacity may vary depending on the feedstock present in the silo.

Metering Vessel (Ref. No. 2)

Description:
Material from the Raw Feedstock Storage Silos (Ref 1A) is metered at a rate of 41.7 pounds per minute to the Pre-treatment Chamber (Ref. 3) by a variable speed auguring system (material from storage silo 1B will not require pre-treatment). The Metering Vessel allows for the precise control of feedstock volume being fed to the Pre-Treatment Chamber (Ref. 3).

Input:
Material from Raw Feedstock Storage Silo 1A: 41.7 lbs/min (8 hours/day, 5 days/week).

Output:
Material to Pre-Treatment Chamber: 41.7 lbs/min (8 hours/day, 5 days/week).

Specifications:
The Metering Vessel is constructed of 12 gauge sheet welded steel and consist of a feed hopper with a screw conveying system to allow for uniform flow into the Pre-Treatment Chamber (Ref. 3).

The Metering Vessel has an approximate capacity of 670 ft$^3$ (1/2 day using 15 lbs/ft$^3$ as a standard density).

Storage capacity may vary depending on the feedstock present in the silo.

Pre-Treatment Chamber (Ref. No. 3)

Description:
Raw feedstock is metered into the Pre-Treatment Chamber at a rate of 41.7 pounds per minute. Dilute sulfuric acid (1%–2% concentration) is injected from the Dilute Sulfuric Acid Storage Vessel (Ref. 4) at 40° to 100° C. into the chamber at a rate of 250 pounds per minute, simultaneously mixing with the feedstock. The mix ratio is about 4:1 to 6:1 (four to six pounds of 1%–2% concentrated sulfuric acid to every one pound of feedstock). During the continuous feed process, a ten (10) minute retention time in the mixing chamber is maintained to allow the separation of heavy metals from the raw feedstock. The treated feedstock is continuously metered to the Primary Screw Press (Ref. 5A) at a rate of 291.7 pounds per minute.

Input:
Feedstock: 41.7 lbs/min (8 hours/day, 5 days/week).
Dilute Acid (1%–2%): 250 lbs/min (8 hours/day, 5 days/week).

Output:
Material to Primary Screw Press (Ref. 5A): 291.7 lbs/min (8 hours/day, 5 days/week).

Specifications:
The Pre-Treatment Chamber consists of a screw conveyor with a leak proof trough. The Chamber is constructed of acid resistant materials and corrosion proof seals. The material being conveyed has a 10 minute retention time in the Pre-Treatment Chamber and is sized accordingly (about 20 feet long).

The Pre-Treatment Chamber has an approximate capacity of 66.7 ft$^3$ (500 gallons), the capacity may vary depending on the feedstock present in the silo.

Dilute Sulfuric Acid Storage Vessel (Ref. No. 4)

Description:
Storage for dilute sulfuric acid (1%–2% concentration). The dilute sulfuric acid is piped to the Pre-Treatment Chamber (Ref. 3) at a rate of 250 pounds per minute. Recycled dilute sulfuric acid reclaimed from the Primary Screw Press (Ref 5A) is returned at a rate of 187.5 pounds per minute (based on removal of 75% of moisture). The Dilute Sulfuric Acid Storage Vessel is equipped with a bleeder valve in order to remove a portion of the solution and pipe it at a rate of 27.4 lbs/min to the Dilute Sulfuric Acid Neutralization Vessel (Ref. 8). The Dilute Sulfuric Acid Storage Vessel is designed to hold about 8000 gallons.

Input:
Recycled Dilute Acid: 187.5 lbs/min (8 hours/day, 5 days/week).
Make-up Dilute Acid: 36.0 lbs/min (8 hours/day, 5 days/week).
Make-up Water: 54.0 lbs/min (8 hours/day, 5 days/week).

Output:
Liquid to Pre-Treatment Chamber (Ref. 3): 250 lbs/min (8 hours/day, 5 days week).
Liquid to Dilute Sulfuric Acid/Lime Neutralization Vessel (Ref. 8): 27.4 lbs/min (8 hours/day, 5 days/week).

Specifications:
The Dilute Sulfuric Acid Storage Vessel is constructed of an acid resistant, premium/iso. resin, with top and side manways and an epoxy coated ladder with no cage.

The Dilute Sulfuric Acid Vessel has a capacity of 1,070 ft$^3$ (8,000 gallons).

Primary Screw Press (Ref. No. 5A)

Description:
Neutralized feedstock is discharged to the Primary Screw Press at a rate of 291.7 pounds per minute from the Pre-Treatment Chamber (Ref. 3). A controlled compression rate allows the removal of 60%–80% of the dilute sulfuric acid at a rate of about 187.5 pounds per minute (based on a 75% moisture removal rate). The dilute sulfuric acid is then returned to the Dilute Acid Storage Vessel (Ref. 4) for reuse. The action of the Screw Press compresses the solids which are then pulverized and conveyed to the Secondary Screw Press (Ref. 5B) by a blending screw conveyor with water inlets to allow the material to be washed as it is transported to the Secondary Screw Press (Ref. 5B).

Input:
291.7 lbs/min (8 hours/day, 5 days/week).

Output:
Liquid to Dilute Sulfuric Acid Storage Vessel: 187.5 lbs/min (8 hours/day, 5 days/week).
Solids to Secondary Screw Press: 104 lbs/min (8 hours/day, 5 days/week).

Specifications:
The Primary Screw Press is constructed of corrosion resistant materials and shall have an approximate 10 minute retention time. A minimum of 60% liquid extraction is required.

Secondary Screw Press (Ref. No. 5B)

Description:
Neutralized feedstock is conveyed from the Primary Screw Press (Ref. 5A) to the Secondary Screw Press at a rate of 104 pounds per minute. Water is piped from the Water Holding Vessel (Ref. 29B) into a screw conveyor at a rate of 187.5 pounds per minute and mixed with the solids from the Primary Screw Press (Ref. 5A). The mixing of the solids and water allows for the last traces of sulfuric acid to be removed from the solid material. The Secondary Screw Press compresses the mixture allowing the removal of 60%–80% of the water at a rate of about 187.5 pounds per minute. The water is then returned to the Water Holding Vessel (Ref. 29B). The action of the Secondary Screw Press compresses the solids which are then pulverized and conveyed to the Dryer (Ref. 6).

Input:
Solids from Primary Screw Press (Ref. 5A): 104 lbs/min (8 hours/day, 5 days/week).
Water from Water Holding Vessel (Ref. 29B): 187.5 lbs/min (8 hours/day, 5 days/week).

Output:
Solids to Dryer (Ref. 6): 104 lbs/min (8 hours/day, 5 days/week).
Water to Water Holding Vessel (Ref. 29B): 187.5 lbs/min (8 hours/day, 5 days/week).

Specifications:
The Secondary Screw Press is constructed of corrosion resistant materials and shall have an approximate 10 minute retention time. A minimum of 60% liquid extraction is required.

Dryer (Ref. No. 6)

Description:
Material is received at a rate of about 104 pounds per minute from the Secondary Screw Press (Ref. 5B) with about a 30%–50% moisture content. The dryer has a flow and capacity rating of 4.00 tons per hour, producing a product with a moisture content of about 5%–10%. The dried material has a light fluff consistency. The dried material is then pneumatically conveyed to the Processed Feedstock Storage Vessel (Ref. 7).

Input:
Solids from Secondary Screw Press (Ref. 5B): 104 lbs/min (8 hours/day, 5 days/week).

Output:
Solids to Processed Feedstock Storage Silo (Ref. 7): 45.0 lbs/min (8 hours/day, 5 days/week).
Liquid Lost to Drying Process: 59.1 lbs/min (8 hours/day, 5 days/week).

Specifications:
4.00 TPH throughput.
Keeping with design requirements of air, temperature and retention time variables for proper drying and cooling limits.
With accessible air controls by multiple fans, air locks and internal duct work.
Woven or slotted plate apron design to suit product mixture.
Standard construction (Food grade construction is not required).
Two pass design with zoned fully controlled drying, mixing product for uniformity and controlling heat loss.

Processed Feedstock Storage Vessel (Ref. No. 7)

Description:
Processed feedstock is pneumatically conveyed from the Dryer (Ref. 6) to the storage vessel at a rate of 45.0 pounds per minute. The vessel is designed to hold 25 tons of feedstock (about a two and one half (2½) day supply). Material is metered to the Hydrolysis System (Ref. 12) at the precise rate of 27.8 pounds per minute.

Input:
Solids from Dryer (Ref. 6): 45.0 lbs/min (8 hours/day, 5 days/week).

Output:
Solids to Hydrolysis System (Ref. 12): 27.8 lbs/min (24 hours/day, 5 days/week, alternating one hour operating and one hour resting).

Specifications:
The Processed Feedstock Storage vessel is constructed of corrosion resistant, 12 gauge sheet welded steel and has a capacity of about 2½ day storage area (using 15 lbs/ft$^3$ as a standard).
Storage capacity may vary depending on the density of the feedstock present in the silo. The silo will maintain the 5% to 10% moisture level required in the feedstock.

Dilute Sulfuric Acid Neutralization Vessel (Ref. No. 8)

Description:
Heavy metals and particulates settle to the bottom of the Dilute Sulfuric Acid Storage Vessel (Ref. 4). Dilute sulfuric acid (1%–2% concentration) along with the contaminants is piped from the bottom of the Dilute Sulfuric Acid Storage Vessel (Ref. 4) into the Dilute Sulfuric Acid Neutralization Vessel at a rate of 27.5 pounds per minute. On a weekly basis, the contaminated acid solution is treated with 1020 pounds of lime. The lime reacts with the acid, capturing the heavy metals, forming gypsum. The liquid is piped to the Gypsum Belt Press (Ref. 10) at a rate of 142.8 pounds per minute.

Input:
Solution from Dilute Sulfuric Acid Storage Vessel (Ref. 4): 27.5 lbs/min (8 hours/day, 5 days/week).
Lime from Lime Holding Vessel (Ref 9): 1,020 lbs of lime is manually added to the vessel once a week. While all 1,020 lbs is added at once, on average, the lime is added at 2.1 lbs/min (8 hours/day, 1 day on weekend).

Output:
Solution to Gypsum Belt Press (Ref. 10): 142.8 lbs/min (8 hours/day, 1 day on weekend).

Specifications:

A premium/iso resin, top and side manway, epoxy coated ladder (no cage) with an 8000 gallon capacity, being of a nominal 10'4" ID×16'7" height flat bottom with a minimum of four hold-down lugs and lift legs.

Lime Holding Vessel (Ref. No. 9)

Description:

This vessel holds lime for the periodic neutralization and capture of heavy metals from the dilute sulfuric acid. The lime, in either a liquid or dry form, is manually added to the Dilute Sulfuric Acid Neutralization Vessel (Ref. 8) at an approximate rate of 2.1 pounds per minute (1,020 pounds per week).

Input:

Lime: Replaced as needed.

Output:

Lime to Dilute Sulfuric Acid Neutralization Vessel (Ref. 8): 1,020 lbs of dry lime is manually added to the Dilute Sulfuric Acid Neutralization Vessel (Ref. 8) once a week. While all 1,020 lbs is added at once, on average, the lime is added at 2.13 lbs/min (8 hours/day, one day on weekend).

Specifications:

If the lime is purchased in bulk, the vessel holds 1,500 pounds of lime in a dry, form with a manual discharge chute.

If purchased in sacks, the vessel will be deleted and sacks of dry lime are to be stacked on pallets.

Gypsum Belt Press (Ref. No. 10)

Description:

Liquid is pumped from the Dilute Sulfuric Acid Neutralization Vessel (Ref. 8) to the Gypsum Belt Press at a rate of 142.8 pounds per minute. The gypsum is separated from the neutralized liquid and conveyed to a holding vessel at a rate of 3.91 pounds per minute. The neutralized liquid is piped at a rate of 136.6 pounds per minute to the Neutralized Water Storage Vessel (Ref. 11).

Input:

Solution from Dilute Sulfuric Acid Neutralization Vessel (Ref. 8): 142.8 lbs/min (8 hours/day, 1 day on weekend).

Output:

Gypsum: 3.9 lbs/min (8 hours/day, 1 day on weekend).

Water to Neutralized Water Storage Vessel (Ref. 11): 138.9 lbs/min (8 hours/day, 1 day on weekend).

Specifications:

High pressure belt press with nip rollers to dewater neutralized mixture and separate water from gypsum. Produced a product with a moisture content of about 50%.

Neutralized Water Storage Vessel (Ref. No. 11)

Description:

Filtered liquid from the Water Storage Vessel (Ref. 29A) and the Gypsum Belt Press (Ref. 10) is dispensed into the Neutralized Water Storage Vessel when required to maintain the balance of the dilute sulfuric acid required in the pre-treatment process. The Neutralized Water Storage Vessel has a capacity of 3000 gallons.

Input:

Water from Gypsum Belt Press (Ref. 10): 136.6 lbs/rain (8 hours/day, 1 day on weekend).

Water from Water Storage Vessel (Ref. 29A): 26.6 lbs/min (8 hours/day, 5 days/week).

Output:

Water to Dilute Sulfuric Acid Storage Vessel (Ref. 4): 54.0 lbs/min (8 hours/day, 5 days/week).

Specifications:

Isophthallic resin, top and side manways, epoxy coated ladder (no cage) sized to hold 8000 gallons and being of a nominal size as 7'6" ID×10' high. Flat bottom with a minimum of four hold-down lugs and lift legs.

Hydrolysis System (Hydrolyzer) (Ref. No. 12)

Description:

The purpose of the Hydrolysis System is to break down the solid feedstock into cellulose and hemicellulose. Feedstock is metered from either storage vessel (Ref 7 or 1B) at a rate of 27.8 pounds per minute. Concentrated sulfuric acid (70% concentration) is automatically injected into the Hydrolyzer at a rate of 27.8 pounds per minute from the Concentrated Sulfuric Acid Storage Vessel (Ref. 30). In a continuous feed system, the feedstock and acid are continuously blended for a resident time of about ten minutes. The two materials form a gel which is discharged from the Hydrolyzer at a rate of 55.6 pounds per minute to the Cooking Vessels (Ref. 13). The Hydrolyzer is automatically flushed with 88° C. water to clean the unit and transfer any remaining residue to the Cooking Vessel. It takes about one hour to meter the feedstock through the Hydrolysis System, flush the system and fill the Cooking Vessel (Ref. 13). The Hydrolysis System operates one hour and fills one Cooking Vessel. The system then sits idle for one hour before beginning its process again to fill the second Cooking Vessel.

Input:

Feedstock from Storage Vessels (Ref. 7 or 1B): 27.8 lbs/rain (24 hours/day, 5 days/week, alternating one hour operating and one hour resting).

Concentrated Sulfuric Acid from Concentrated Sulfuric Acid Storage Vessel (Ref. 30): 27.8 lbs/rain (24 hours/day, 5 days/week, alternating one hour operating and one hour resting).

Output:

Gel to Cooking Vessel (Ref. 13): 55.6 lbs/min (24 hours/day, 5 days/week, alternating one hour operating and one hour resting)

Specifications:

The Hydrolysis System consists of a screw conveyor with a leak proof trough.

The chamber is constructed of acid resistant materials and corrosion proof seals.

The material being conveyed has a 10 minute retention time in the Hydrolysis System and is sized accordingly (about 15 feet long).

The Hydrolysis System has an approximate capacity of 55.6 lbs/min.

Cooking Vessel (Quantity 2) (Ref. No. 13)

Description:

Each Cooking Vessel is operated independently, constructed of polyethylene resins and sized at 1250 gallons each (about 6' in diameter by 6'–8" in height). Each tank is equipped with agitators and heat tracing to maintain the 95° C.–99° C. approximate temperature required for reaction. Each tank is covered with 2" thick polyurethane insulation to minimize heat loss. The hydrolyzed material is deposited into 790 gallons of 88° C. water. The water flows into the Cooking Vessel from the Water Heater (Ref. 32) at a rate of 111 pounds per minute (13.3 gallons per minute). The ratio of product in the Cooking Vessel is two to four parts water, one part 70% concentrate sulfuric acid and one part feedstock. The residence time in the Cooking Vessel is two hours, plus one hour fill time and one hour discharge time. The purpose of the two hour residence time is to further break down the feedstock material and to convert the cellulose into sugars. At the end of the two hour residence period, the vessel is emptied at a rate of 166.7 pounds per minute into Holding Vessel #1 (Ref. 14). After being emptied, the vessel is then ready to receive product from the Hydrolysis System (Ref. 12).

Input:

Gel from Hydrolysis System (Ref. 12): 55.6 lbs/min (24 hours/day, 5 days/week, alternating one hour operating and one hour resting).

Water from Water Heater (Ref. 32): 111 lbs/min (24 hours/day, 5 days/week, alternating one hour operating and one hour resting).

Output:

Liquid Product to Holding Vessel #1 (Ref. 14): 166.7 lbs/min (24 hours/day, 5 days/week, alternating one hour operating and one hour resting).

Specifications:

6' ID×80" high, iso. resin, dished bottom, steel legs for 2' clearance, flanged top w/bolt down cover, 18" QA manway, steel agitator support assembly, heat tracing to maintain 88° C., and 2" thick polyurethane insulation.

Holding Vessel #1 (Ref. No. 14)

Description:

Each Cooker Vessel (Ref. 13) evacuates to this tank at a rate of 166.7 pound per minute for one hour. Due to the 2 hour residence time of the Cooking Vessel (Ref 13), there is a one hour lag time between fills for Holding Vessel #1. The Holding Vessel allows the material to cool and enables the Cooking Vessel to be charged with new material. The tank has a 600 gallon capacity, constructed of polyethylene and has no insulation. The tank is sized to discharge at a steady flow rate of 83.3 pounds per minute to the Filter Press (Ref. 15).

Input:

Liquid from Cooking Vessel (Ref. 13): 166.7 lbs/min (24 hours/day, 5 days/week, alternating one hour operating and one hour resting).

Output:

Liquid to Filter Press (Ref. 15): 83 lbs/min (24 hours/day, 5 days/week).

Specifications:

42" I.D.×82" High, Iso. resin, 30° cone bottom, steel legs for 2' clearance, dome (closed) top w/18" QA manway. Flat bottom with a minimum of four hold-down lugs and lift legs.

Filter Press (Ref. No. 15)

Description:

Material from the Holding Vessel #1 (Ref. 14) is piped to the Filter Press at a rate of 83 pounds per minute. The membrane filter press is employed to remove the suspended solids from the liquid mixture. The resulting solids have about 30 to 50% moisture content and are deposited at a rate of 5.2 pounds per minute into the Lignin Holding Vessel (Ref. A) to await washing. The liquid material from the press is piped at a rate of 78 pounds per minute to the Acid Recovery Storage Vessel (Ref. 16).

Input:

Liquid from Holding Vessel #1 (Ref. 14): 83 lbs/min (24 hours/day, 5 days/week).

Output:

Solids to Lignin Holding Vessel (Ref. A): 5.2 lbs/min (24 hours/day, 5 days/week).

Liquid to Acid Recovery Storage Vessel (Ref. 16): 78 lbs/min (24 hours/day, 5 days/week).

Specifications:

A membrane filter press to accept 83 lbs/min of liquid. Complete with press frame, PLC control system, drip trays, membrane plates pack with manifold—automatic controls including panel, wiring, etc.

Acid Recovery Storage Vessel (Ref. No. 16)

Description:

The liquids from the Filter Press (Ref. 15) are pumped to the Acid Recovery Storage Vessel at a rate of 78 pounds per minute. The Acid Recovery Storage Vessel allows the Acid Recovery System (Ref. 17) to operate 24 hours a day, seven days a week (the Pre-Treatment Stage and the Hydrolysis Process operates 5 days a week). The Acid Recovery Storage Vessel is designed to hold 19,000 gallons (2 days worth) of liquid product for the Acid Recovery System (Ref. 17). A storage vessel of this size simply allows the Acid Recovery System (Ref. 17) to operate on weekends. The liquid product is piped to the Acid Recovery System (Ref. 17) at a rate of 55.8 pounds per minute.

Input:

Liquid from Filter Press (Ref. 15): 78 lbs/min (24 hours/day, 5 days/week).

Output:

Liquid to Acid Recovery System (Ref. 17): 55.8 lbs/min (24 hours/day, 7 days/week).

Specifications:

11'-9" ID×24'-2" High iso. resin top and side manways epoxy coated ladder (no cage). Flat bottom with a minimum of four hold-down lugs and lift legs.

Acid Recovery System (Ref. No. 17)

Description:

The liquids from the Acid Recovery Storage Vessel (Ref. 16) are pumped to the Acid Recovery System at a flow rate of 55.8 pounds per minute. Water is also piped into the Acid Recovery System from the Water Storage Vessel (Ref. 29A) at a rate of 118 pounds per minute. In the Acid Recovery System, about 96–99% of the sulfuric acid and about 92–99% of the sugars are recovered and separated into two distinct product streams. The sulfuric acid solution (now concentrated to 5% sulfuric acid) is pumped at a rate of 116.2 pounds per minute to the Evaporator (Ref. 18). If the Pre-Treatment Process is operating, the acid solution is piped to the Dilute Sulfuric Acid Storage Vessel (Ref. 4) at a rate of 36.0 pounds per minute and to the Evaporator at a rate of 80 pounds per minute. The sugar solution (concentrated to 9–12% sugar) is pumped at a rate of 58.1 pounds per minute to the Holding Vessel #2 (Ref. 19) for later introduction to the Reverse Osmosis Filter (Ref. 20).

Input:

Liquid from Acid Recovery Storage Vessel (Ref. 16): 55.8 lbs/rain (24 hours/day, 7 days/week).

Water from Water Storage Vessel (Ref. 29A): 118.5 lbs/min (24 hours/day, 7 days/week).

Output:

Sugar Solution to Holding Vessel #2 (Ref. 19): 58.10 lbs/min (24 hours/day, 7 days week).

Acid Solution to Evaporator (Ref. 18): 116.2 lbs/min (from hours 8–24, 5 days/week and 24 hours a day on weekends).

During 8 hours of Pre-Treatment Process Operation:

Input:

Liquid from Acid Recovery Storage Vessel (Ref. 16): 55.8 lbs/min (24 hours/day, 7 days/week).

Water from Water Storage Vessel (Ref. 29A): 118.5 lbs/min (24 hours/day, 7 days/week).
Output:
Sugar Solution to Holding Vessel #2 (Ref. 19): 58.1 lbs/min (24 hours/day, 7 days/week).
Acid Solution to Evaporator (Ref. 18): 80 lbs/min (from hours 0–8, 5 days/week).
Acid Solution to Dilute Acid Storage Vessel (Ref. 4): 36 lbs/min (from hours 0–8, 5 days/week).
Specifications:
Ion-exchange system designed to process the sugar/acid/water solution for 24 hours/day, 7 days/week, is available from Advanced Separation Technologies Incorporated, Lakeland, Fla. (Model No. ISEP LC2000). A strongly acidic ion-exchange resin (Finex SC16G, 310 micron size) from Advanced Separation Technologies is employed.

Evaporator (Ref. No. 18)

Description:
The acid solution is pumped at a rate of 116.2 pounds per minute from the Acid Recovery System (Ref. 17). Water is evaporated from the sulfuric acid, allowing the acid concentration to return to 70% (its original state). The concentrated acid is pumped at a rate of 8.3 pounds per minute to the Concentrated Sulfuric Acid Storage Vessel (Ref. 30) for reuse. The evaporated water is captured and condensed by the Evaporator and piped at a rate of 107.9 pounds per minute to the Water Storage Vessel (Ref. 29) for system reuse. During the 8 hours when the PreTreatment Process is operating, the volumes at this station are follows: 1) acid solution input: 80 pounds per minute, 2) concentrated acid output: 5.7 pounds per minute, 3) water output: 74.5 pounds per minute.
Input:
Acid Solution from Acid Recovery System (Ref. 17): 116.2 lbs/min (from hours 8–24, 5 days/week and 24 hours a day on weekends).
Output:
Concentrated Acid Solution to Concentrated Sulfuric Acid Storage Vessel (Ref. 30): 8.30 lbs/rain (from hours 8–24, 5 days/week and 24 hours a day on weekends).
Water to Water Storage Vessel (Ref. 29): 107.9 lbs/min (from hours 8–24, 5 days/week and 24 hours a day on weekends).
During 8 hours of Pre-Treatment Process Operation:
Input:
Acid Solution from Acid Recovery System (Ref. 17): 80 lbs/rain (from hours 0–8, 5 days/week).
Output:
Concentrated Acid Solution to Concentrated Sulfuric Acid Storage Vessel (Ref. 30): 5.7 lbs/rain (from hours 0–8, 5 days/week).
Water to Water Storage Vessel (Ref. 29): 74.5 lbs/min (from hours 0–8, 5 days/week).
Specifications:
Plate evaporator or equal to remove the $H_2O$ from the acid in the liquid stream returning the $H_2SO_4$ to a minimum of 70% concentration.

Holding Vessel #2 (Ref. No. 19)

Description:
The sugar solution is piped from the Acid Recovery System (Ref. 17) at a rate of 58.1 pounds per minute to Holding Vessel #2. The vessel is designed to receive the sugar/water solution from the Acid Recovery System (Ref. 17) and provides the source for a continuous stream of solution to the Reverse Osmosis Filter (Ref. 20). The sugar solution is piped from the Holding Vessel (capacity of 600 gallons) to the Reverse Osmosis Filter at a rate of 58.1 pounds per minute.
Input:
Sugar Solution from Acid Recovery System (Ref. 17): 58.1 lbs/min (24 hours/day, 7 days/week).
Output:
Sugar Solution to Reverse Osmosis Filter (Ref. 20): 58.1 lbs/min (24 hours/day, 7 days/week).
Specifications:
48" I.D.×80" High, Iso. resin, fiat bottom, closed top, with 18" QA manway. Flat bottom with a minimum of four hold-down lugs and lift legs.

Reverse Osmosis Filter (Ref. No. 20)

Description:
The sugar solution is piped from Holding Vessel #2 (Ref. 19) to the Reverse Osmosis Filter at a rate of 58.1 pounds per minute. The purpose of the Reverse Osmosis Filter is to increase the sugar concentration in the solution. The filter increases the sugar concentration form 9% sugar to about 15% sugar (the optimum sugar concentration for fermentation). The sugar solution is then piped to the Ammonia and pH Balancing System at a rate of 34.1 pounds per minute. The extracted water is pumped to the Water Storage Vessel (Ref. 29A) at a rate of 24.0 pounds per minute.
Input:
Sugar Solution from Holding Vessel #2 (Ref 19): 58.1 lbs/rain (24 hours/day, 7 days/week).
Output:
Sugar Solution to Ammonia and pH balancing System (Ref. 21): 34 lbs/min (24 hours/day, 7 days/week).
Water to Water Storage Vessel (Ref. 29A): 24 lbs/min (24 hours/day, 7 days/week).
Specifications:
A nano-filtration system designed specifically to concentrate the sugar/water solution.

Ammonia and pH Balancing System (Ref. No. 21)

Description:
The Ammonia and pH Balance System is comprised of an ammonia storage vessel and in-line injectors for the introduction of ammonia into the sugar solution. The sugar solution is piped to the Ammonia and pH Balancing System at a rate of 34 pounds per minute from the Reverse Osmosis Filter (Ref. 20). Precise amounts of ammonia are automatically injected into the solution at an approximate rate of 0.047 pounds per minute, while the pH balance is rigorously monitored. The ammonia stabilizes the pH balance to about six (6), creating an ideal environment for the yeast to react with the sugars. The entire process takes place as the solution flows at a rate of 34 pounds per minute to the Yeast Injection System (Ref. 22).
Input:
Sugar Solution from Reverse Osmosis Filter (Ref. 20): 34 lbs/min (24 hours/day, 7 days/week).
Ammonia from Ammonia Storage Vessel: 0.1 lbs/min (24 hours/day, 7 days/week).
Make-up Ammonia Required: 484 lbs/week.
Output:
Sugar/Ammonia Solution to Yeast Injection System (Ref. 22): 34 lbs/min (24 hours/day, 7 days/week).
Specifications:
A value control unit to inject precise amounts of ammonia into the flow line of sugar, water, and trace acid. Unit includes pH balance sensors to monitor the pH balance informing the control injector to add proper balance of ammonia to the stream.

Yeast Injection System (Ref. No. 22)

Description:

The Yeast Injection System is an on-line system similar to the Ammonia and pH Balancing System (Ref. 21). The Yeast Injection System is comprised of a yeast storage vessel and an in-line injector for the introduction of yeast into the sugar/ammonia solution. The sugar solution is piped to the Yeast Injection System at a rate of 34 lbs/min from the Ammonia and pH Balancing System (Ref. 21). Precise amounts of yeast are automatically injected into the solution at an approximate rate of 0.8 pounds per minute. The entire yeast injection process takes place as the solution flows at a rate of 35 pounds per minute to Holding Vessel #3 (Ref. 23).

Input:

Sugar/Ammonia Solution from Ammonia and pH Balancing System (Ref. 21): 34 lbs/min (24 hours/day, 7 days/week).

Yeast from Yeast Storage Vessel: 0.853 lbs/min (24 hours/day, 7 days/week).

Make-up Yeast Required: As yet undetermined. If all yeast can be recaptured by the Yeast Filter (Ref. 25), very little make-up yeast will be required.

Output:

Sugar/Ammonia/Yeast Solution to Holding Vessel #3 (Ref. 23): 35 lbs/min (24 hours/day, 7 days/week).

Specifications:

A value control unit to inject precise amounts of yeast in the flow line of sugar and water for fermentation. 1000 gallon capacity, 6' I.D.×5'6" High, iso. resin, flat bottom, closed top, epoxy coated ladder (no cage).

Holding Vessel #3 (Ref. No. 23)

Description:

The Sugar/Ammonia/Yeast solution is piped into Holding Vessel #3 from the Yeast Injection System (Ref. 22) at a rate of 35 pounds per minute. The Holding Vessel is designed to store 3,000 gallons of solution. The size of the Holding Vessel makes it possible to fill the Fermentation Vessel (Ref. 24) with an entire days worth of solution in 12 hours. The solution is piped from Holding Vessel #3 to the Fermentation Vessel (Ref. 24) at a rate of 70 pounds per minute for 12 hours.

Input:

Sugar/Ammonia/Yeast Solution from Yeast Injection System (Ref. 22): 35 lbs/min (24 hours/day, 7 days/week).

Output:

Sugar/Ammonia/Yeast Solution to Fermentation Vessel (Ref. 24): 70 lbs/min (12 hours/day, 7 days/week).

Specifications:

3,000 gallon capacity, 7'-6" I.D.×10'-1" High, prem/iso. resin w/Nexus veil, including 24" side and top manways, and epoxy coated ladder (no cage).

Fermentation Vessel (Quantity 3) (Ref. No. 24)

Description:

Sugar/Ammonia/Yeast solution piped from Holding Vessel #3 (Ref. 23) into the Fermentation Vessel at a rate of 70 pounds per minute. The Fermentation Vessel has a capacity of 6500 gallons. When the Fermentation Vessel is filled, the mixture is heated to 33° to 36° C. to begin the fermentation reaction. During the fermentation process, the sugars are converted to ethanol by the yeast microbes. Heat will be generated by the reaction once it begins. The Chillier Coil (Ref. 27) is used to maintain the temperature of the mixture at about 33° to 36° C. and thereby prevent heat escalation. After about 48 hours of retention time in the Fermentation Vessel, the fermented beer solution is piped to the Yeast Filter and Distillation Holding Vessel (Ref. 25) at a rate of 419.8 pounds per minute for about 2 hours. The Fermentation Vessel is then steam cleaned and prepared for another batch.

Input:

Sugar/Ammonia/Yeast Solution from Holding Vessel #3 (Ref. 23): 70 lbs/min (12 hours/day, 7 days/week).

Output:

Fermented Beer Solution to Yeast Filter and Distillation Holding Vessel (Ref. 25): 419.8 lbs/min (2 hours/day, 7 days/week).

Specifications:

6,500 gallon capacity, 10'-4" I.D.×11' High, iso. resin, flat bottom. closed top 24" side and top manways and epoxy coated ladder (no cage).

Yeast Filter and Distillation Holding Vessel (Ref. No. 25)

Description:

The Yeast Filter and Distillation Holding Vessel consists of a trap filter to capture the yeast and return it to the Yeast Injection system (Ref. 22) and a Distillation Holding Vessel to regulate flow into the Distillation Column (Ref. 26) and provide a short evacuation time for the Fermentation Vessels (Ref. 24) (about 2 hours). The fermented beer solution is piped from the Fermentation Vessel (Ref. 24) to the Yeast Filter at a rate of 419.8 pounds per minute. The trap filter removes the yeast from the fermented beer and pumps the yeast to the Yeast Injection System (Ref. 22) at a rate of 10.2 pounds per minute. The remaining fermented beer solution is piped into the Distillation Holding Vessel at a rate of 409.6 pounds per minute. The Yeast Filter and Distillation Holding Vessel regulates the flow of fermented beer solution into the Distillation Column (Ref. 26) at a rate of 34 pounds per minute.

Input:

Fermented Beer from Fermentation Vessel (Ref. 24): 419.8 lbs/min (2 hours/day, 7 days/week).

Output:

Yeast to Yeast Injection System (Ref. 22): 10.2 lbs/min (2 hours/day, 7 days/week).

Fermented Beer to Distillation Column (Ref. 26): 34 lbs/min (21 hours/day, 7 days/week).

Specifications:

6,500 gallon capacity, 10'-4" I.D.×11' High, iso. resin, flat bottom, closed top 24" side and top manways and epoxy coated ladder (no cage).

Distillation Column (Ref. No. 26)

Description:

Fermented beer is piped from the Yeast Filter and Distillation Holding Vessel to the Distillation Column at a ram of 34.1 pounds per minute. The Distillation Column accepts the fermented beer at 12%–14% ethanol (by volume) and concentrates the ethanol to 99.7% ethanol Coy volume). The first step of the distillation process concentrates the ethanol to about 94% by volume. The second step removes almost all of the remaining water with a desiccant.

Conventional distillation is used in the first step of the dehydration column. The 94% ethanol/6% water vapor from the distillation step is then passed through a molecular sieve column, where the water is adsorbed onto the surface of the molecular sieve material. Once the molecular sieve material is saturated with water, it is regenerated by drying with hot nitrogen.

The Distillation Column consists of a beer still, dehydration column and entrainer recovery column. With this particular application, the dehydration column is used to provide 60% of the heat required for the beer still. The system is designed to allow for the beer still and the dehydration column to be run independently. The ethanol is piped from the Distillation Column to the Ethanol Storage Vessel (Ref. 28) at a rate of 4.6 pounds per minute (based on a standard output of 100 gallons per ton of dry feedstock). The output flow rate will vary from 60–120 gallons per ton dry feedstock, depending on the quality of the feedstock used. The remaining stillage from the Distillation Column is pumped at a rate of 1.5 pounds per minute to a holding area to await sale as cattle feed. The water in the solution is evaporated off at a rate of 28 pounds per minute. In the future, the evaporated water may be captured and condensed for reuse.
Input: Fermented Beer from Yeast Filter and Distillation Holding Vessel (Ref. 34 lbs/rain (24 hours/day, 7 days/week).
Output:
Ethanol to Ethanol Storage Vessel (Ref. 28): 4.6 lbs/min (24 hours/day, 7 days/week).
Stillage to Holding Area: 1.5 lbs/min (24 hours/day, 7 days/week).
Water Loss to Evaporation: 28 lbs/min (24 hours/day, 7 days/week).
Specifications:
Distillation Column consists of the following equipment: Degasser Condenser, Degasser Reboiler, Feed Preheater, Beer Still, Dehydration Column, Condenser/Reboiler, Final Condenser, Condenser, Decanter, Vent Condenser, Entrainer, Recovery Column, Reboiler and Ethanol Cooler.
Maximum input shall be 9 gallons per minute.
Size: 16 inch stripper and rectifier.
Ethanol to be used as fuel shall have less than 0.5% water.
Steam requirements shall be 1000 lbs/hr.

Chiller Coil (Ref. No. 27)

Description:
The Chiller Coil is a basic heat exchanger for the heating and removal of heat from the Fermentation Vessels (Ref. 24). The coil utilizes steam heat from the boiler to begin the fermentation reaction. After the reaction begins, the Chillier Coil utilizes cool water from a lagoon for heat removal from the Fermentation Vessels. The Chiller Coil maintains the temperature of the Fermentation Vessel (Ref. 24) at 36° C.
Input:
Water from Lagoon: As Required (24 hours/day, 7 days/week).
Steam from Boiler: 50 lbs psig as required.
Output:
Water to Lagoon: As Required (24 hours/day, 7 days/week).
Steam to Boiler: 50 lbs psig as required.
Specifications:
The water requirements for the Chiller Coil are delivered as required.
The boiler steam requirements for the Chiller Coil are provided as required.

Ethanol Storage Vessel (Ref. No. 28)

Description:
Ethanol from the Distillation Column (Ref. 26) is piped to the Ethanol Storage Vessel at a rate of 4.6 pounds per minute (using 100 gallons per ton dry feedstock as standard). The Ethanol Storage Vessel is emptied every week to a tanker truck at an approximate rate of 340 pounds per minute. All storage tanks are ASME certified and exceed any and all state and local codes and industrial regulations as well as EPA and all other environmental agencies. Because of the material contained, a 110% containment barrier as set forth by codes and regulations to capture any spill or purgement of material is specified.
Input:
Ethanol from Distillation Column (Ref. 26): 4.6 lbs/min (24 hours/day, 7 days/week).
Output:
Ethanol to Tanker Truck: 340 lbs/min (2 hours/day, once a week).
Specifications:
10'4"×13'5" high, Premium 470 resin/iso., flat bottom, closed top, side and top manways, with epoxy coated ladder. Flat bottom with a minimum of four hold-down lugs and lift legs.

Water Storage Vessel (Ref. No. 29A)

Description:
Clean water used in the Ethanol Production Process, the Pre-Treatment Process and in the facility is stored in the Water Storage Vessels. The water will be piped to various locations as needed. Approximate water flows are listed as follows:
Input:
Water from Reverse Osmosis Filter (Ref. 20): 24 lbs/min (24 hours/day, 7 days/week).
Water from Evaporator (Ref. 18): 74.5 lbs/min (during hours 0–8, 5 days a week).
Water from Evaporator (Ref. 18): 107.9 lbs/min (during hours 8–24 and on weekends).
Make-up Water: 408,000 lbs/week.
Output:
Water to Neutralized Water Storage Vessel (Ref. 11): 26.6 lbs/min (8 hours/day, 5 days/week).
Water to Water Heater (Ref. 32): 111 lbs/rain (24 hours/day, 5 days/week alternating one hour operating, one hour resting).
Water to Acid Recovery System (Ref. 17): 118 lbs/min (24 hours/day, 7 days/week).
Specifications:
11'–9" I.D.×31'–7" high, isophthallic resin, top & side 24" manways, epoxy coated ladder and cage. Flat bottom with a minimum of four hold-down lugs and lift legs. Approximate capacity of vessel is 25,600 gallons.

Water Storage Vessel (Ref. No. 29B)

Description:
Water circulated in the Pre-Treatment Process is stored in the Water Storage Vessel (Ref. 29B). The water is used to remove any trace heavy metals and acid left in the pre-treated feedstock. The water is piped to the Secondary Screw Press (Ref. 5B) at a rate of 187.5 pounds per minute. The water is then returned from the Secondary Screw Press at a rate of 187.5 pounds per minute. Periodically, the water may need to be neutralized with about 20 pounds of lime. Testing will determine the exact number of days between neutralization.
Input:
Water from Secondary Screw Press (Ref. 5B): 187.5 lbs/min (8 hours/day, 5 days/week).
Output:
Water to Secondary Screw Press (Ref. 5B): 187.5 lbs/rain (8 hours/day, 5 days/week).

Specifications:

(3000 gal.) 7'–6" I.D.×10'–1" high, prem/iso. resin w/Nexus veil. incl. 24" side and top manways, and epoxy coated ladder (no cage). Flat bottom with a minimum of four hold-dour lugs and lift legs.

Concentrated Sulfuric Acid Storage Vessel (Ref. No. 30)

Description:

The Concentrated Sulfuric Acid Vessel serves as a storage vessel for the 70% concentrated sulfuric acid used in the process. The vessel accepts concentrated acid from the Evaporator (Ref. 18) at a rate of 5.7 pounds per minute during the 8 hours of operation of the Pre-Treatment System and 8.30 pounds per minute during the remaining 16 hours of operation and on weekends. The concentrated sulfuric acid is piped from the Concentrated Sulfuric Acid Storage Vessel to the Hydrolysis System (Ref. 12) at a rate of 27.8 pounds per minute, alternating one hour pumping and one hour resting. The Concentrated Acid Storage Vessel is ASME certified and exceeds any and all state and local codes and industrial regulations as well as EPA and all other environmental agencies. Because of the material contained, a 110% containment barrier as set forth by codes and regulations to capture any spill or purgement of material, is specified Input:

Concentrated Sulfuric Acid from Evaporator (Ref. 18): 5.7 lbs/min (from hours 0–8, 5 days/week).

Concentrated Sulfuric Acid from Evaporator (Ref. 18): 8.30 lbs/min (from hours 8–24, 5 days/week and on weekends).

Make-up Sulfuric Acid Required: 22,500 lbs/week.

Output:

Concentrated Sulfuric Acid to Hydrolysis System (Ref. 12): 27.8 lbs/min (24 hours/day, 5 days/week, alternating one hour operating and one hour resting).

Specifications:

10'4" ID×16'7" high, premium/iso resin, top and side manways, epoxy coated ladder and cage. Flat bottom with a minimum of four hold-down lugs and lift legs. Approximate capacity of the vessel is 10,400 gallons.

Waste Water Storage Vessel (Optional) (Ref. No. 31)

Description:

Municipal waste water or sewage may be used as a substitute for water added to the Cooking Vessels (Ref. 13). All bacteria and pathogens are destroyed by the sulfuric acid and >93° C. temperature. Any solids present in the waste water are minimal and in turn will not reduce the BTU rating of the lignin. The high nitrogen content of the waste water not only acts as a fertilizer for the yeast, but also reduces the amount of ammonia required for proper fermentation. The waste water (if used) will be piped to the Water Heater (Ref. 32) at a rate of 111 pounds per minute.

Input:

Waste Water from Source: Delivered in bulk as required. If Waste Water was used exclusively with no clean water as make-up, requirements would be 400,000 lbs/week. On average, the rate of delivery would be 55.6 lbs/rain (24 hours/day, 5 days/week).

Output:

Waste water to Water Heater (Ref. 32): 111 lbs/min (24 hours/day, 5 days/week, alternating one hour pumping and one hour resting).

Specifications:

10'4" ID×16'7" isophthallic resin, top and side 24" manways, epoxy coated ladder (no cage). Flat bottom with a minimum of four hold-down lugs and lift legs. Approximate capacity of the vessel is 10,400 gallons.

Water Heater (Ref. No. 32)

Description:

Clean water from the Water Storage Vessel (Ref. 29A) is piped to the Water Heater at a rate of 111 pounds per minute (if waste water is used, the liquid will be piped from the Waste Water Storage Vessel (Ref. 31) at the same rate). The water is heated to about 88 ° C. and piped to the Cooking Vessels (Ref. 13) at a rate of 111 pounds per minute, pumping one hour and resting one hour.

Input:

Water from Water Storage Vessel (Ref. 29A) or Waste Water Storage Vessel (Ref. 31): 111 lbs/min (24 hours/day, 5 days/week, alternating one hour pumping and one hour resting).

Output:

Water to Cooking Vessel (Ref. 13): 111 lbs/min (24 hours/day, 5 days/week, alternating one hour pumping and one hour resting).

Specifications:

Indirect Fired Hot Water Storage Heater, 36" dia.×52" lg. vertical ASME tank designed for 125 PSIG with a copper coat internal lining and insulation with jacket. Tank capacity is 200 gal.

The unit is furnished with P&T relief valve, pressure and temperature gages, single wall tank heater with non-ferrous tube sheet, self-operating steam control valve, inlet steam strainer, drip trap, and F&T trap. Capacity is 1000 GPH 16° to 88° C., at 100 PSIG steam. This unit will give 1000 GPH continuous duty and 200 gal storage capacity when not in use.

Lignin Holding Vessel (Ref. No. A)

Description:

A simple holding vessel where the pulverized lignin is stored until the material is manually transported to the washing and neutralization area. The lignin is removed from the Filter Press (Ref. 15) at a rate of 5.2 pounds per minute. The lignin is manually loaded into the Secondary Screw Press (Ref. 5B) where it is washed and then dried through the Dryer (Ref. 6) at an approximate rate of 15.6 pounds per minute. After drying, the Lignin carries about a 10,000 to 13,350 BTU per pound rating and is delivered to the Boiler Feedstock Storage Vessel (Ref. B).

Input:

Lignin from Filter Press (Ref. 15): 5.2 lbs/min (24 hours/day, 5 days/week, manual operation).

Output:

Lignin to Secondary Screw Press (Ref. 5B): 15.6 lbs/min (during hours 8–16, 5 days/week).

Specifications:

Portable storage hoppers, dimensions about 6'×6'×5' for a storage capacity of about 180 ft$^3$.

Boiler Feedstock Storage Vessel (Ref. No. B)

Description:

A simple holding vessel for the storage of pulverized lignin and wood chips and/or non-chlorinated plastic. The mixture serves as boiler fuel. The Lignin is conveyed to the Boiler Feedstock Storage Vessel at a rate of 15.6 pounds per minute. The rate in which the boiler fuel is burned will be about 15.8 pounds per minute with a steam production of 3800 pounds of steam per hour.

Input:
Lignin from Dryer (Ref 6): 15.6 lbs/rain (8 hours/day, 5 days/week).
Wood Chips and non-chlorinated plastic: As Required (depending on lignin output).

Output:
Boiler Fuel to Boiler (Ref. C): 15.8 lbs/rain (24 hours/day, 7 days/week).

Specifications:
Boiler feedstock storage hopper, dimensions about 10'× 10'×16' for a storage capacity of about 1600 ft³.

Boiler (Ref. No. C)

Description:
A packaged boiler is used to generate steam and hot water for the system. Elements of the system requiring steam and hot water are the Cooking Vessel (Ref. 13), the Acid Recovery System (Ref. 17); the Fermentation Vessels (Ref. 24) and the Distillation Column (Ref. 26). The steam generating plant is designed to burn a maximum 950 pounds per hour of lignin/wood chip fuel to produce about 3800 pounds of steam per hour delivered at 125 PSIG.

Input:
Boiler Fuel from Boiler Feedstock Storage Vessel (Ref. B): 15.8 lbs/rain (24 hours/day, 7 days/week).

Output:
Steam: 3800 lbs/hour of steam (24 hours/day, 7 days/week).

Specifications:
Boiler System includes fuel feed system, tangential furnace system, HRT boiler pressure vessels, mechanical dust collector, induced draft fan and stack, condensate return and boiler feed system, boiler feed pump and control system, control panel and chemical feed system and water softener.

Summary of Solid Waste Processing System

The process for the treatment of solid waste, waste sludge and scrap tires and producing usable, commercial products is a zero discharge system. The process is fully enclosed and odor controlled. All water is filtered and purified after use and all odor and dust are collected and filtered.

While the present Example describes a ten ton/day process, the same can easily be scaled up to 50–1,000 tons per day. What will change are the flow rams and/or the number of hours that the process will run per day.

Having now fully described this invention, it will be understood by those of ordinary skill in the art that it can be performed within a wide equivalent range of modes of operation as well as other parameters without affecting the scope of the invention or any embodiment thereof.

What is claimed is:
1. A method for producing ethanol from municipal solid waste, comprising the following steps:
(a) obtaining municipal solid waste;
(b) removing tires, bulk ferrous and non-ferrous metals, plastic, glass and rubber from the waste to give a cellulosic component;
(c) shredding the cellulosic component obtained in step (b);
(d) treating the shredded cellulosic component with dilute sulfuric acid at a temperature of 40° to 100° C. to solubilize substantially the remaining heavy metals and give a soluble component and an insoluble component;
(e) removing the soluble component obtained in step (d) from the insoluble component;
(f) drying the insoluble component obtained in step (e);
(g) treating the dried insoluble component obtained in step (f) with about 1:1 concentrated sulfuric acid to insoluble component, by weight, to give a partially hydrolyzed mixture;
(h) diluting the partially hydrolyzed mixture obtained in step (g) with water at a temperature of about 80° to 100° C.;
(i) agitating the diluted mixture obtained in step (h) at about 80° to about 100° C. to give a digested material;
(j) removing the solids from the digested mixture obtained in step (i) to give a filtrate;
(k) separating the filtrate into an acid containing solution and a sugar containing solution;
(l) concentrating the sugar containing solution to about 12–14% sugar;
(m) adjusting the pH of the concentrated sugar containing solution obtained in step (l) to about 6;
(n) fermenting with yeast the solution obtained in step (m) to give a beer; and
(o) recovering the ethanol from the beer.

2. The method of claim 1, wherein in step (e), the soluble component is separated from the insoluble component in a screw press.

3. The method of claim 1, wherein in step (h), the water is waste water or sewage containing organic nitrogen.

4. The method of claim 1, wherein in step (j), the digested mixture is filtered in a filter press.

5. The method of claim 1, wherein in step (k), the filtrate is separated into an acid containing solution and a sugar containing solution by continuous ion-exclusion chromatography.

6. The method of claim 1, wherein in step (k), the filtrate is separated into an acid containing solution and a sugar containing solution by continuous counter current exclusion chromatography.

7. The method of claim 1, wherein in step (l), the sugar containing solution is concentrated to about 12–14% sugar with a reverse osmosis filter.

8. The method of claim 1, wherein in step (m), the pH of the concentrated sugar containing solution obtained in step (l) is adjusted to about 6 by the addition of ammonia.

9. The method of claim 1, wherein in step (o), the yeast is removed from the beer by filtration prior to recovery of the alcohol.

10. The method of claim 1, wherein in step (o), the ethanol is recovered from the beer by distillation.

11. The method of claim 1, wherein in step (h), the partially hydrolyzed material obtained in step (g) is diluted with water of about 80° to 1000° C. to give a solution containing about 4 to 6 parts water to about 1 parts partially hydrolyzed material, by weight.

12. The method of claim 1, wherein the dried insoluble component in step (g) is admixed with sewage sludge or sewage sludge cake before treatment with said concentrated sulfuric acid.

13. A method for producing ethanol from municipal solid waste, comprising the following steps:
(a) obtaining municipal solid waste;
(b) removing tires, bulk ferrous and non ferrous metals, plastic, rubber and glass from the waste to give a cellulosic component;

(c) shredding the cellulosic component obtained in step (b);

(d) treating the shredded cellulosic component with about 1 to 10% sulfuric acid for about 0.25 to 4 hours at a temperature of about 40° to 100° C. to solubilize substantially the remaining heavy metals and give a soluble component and an insoluble component;

(e) removing the soluble component obtained in step (d) from the insoluble component with a screw press;

(f) drying the insoluble component obtained in step (e);

(g) treating the dried, insoluble component obtained in step (f) with about 1:1 concentrated sulfuric acid to insoluble component for about 10 minutes at about 30° to 80° C. to give a partially hydrolyzed mixture;

(h) diluting the partially hydrolyzed mixture obtained in step (g) with water at a temperature of about 80° to 100° C. to give a solution containing about 4 to 6 parts water to about 1 parts partially hydrolyzed material, by weight;

(i) agitating the diluted mixture obtained in step (h) for about 1 to 4 hours at about 80° to about 100° C. to give a digested material;

(j) filtering the digested mixture obtained in step (i) with a filter press to give a filtrate;

(k) separating the filtrate into an acid containing solution and a sugar containing solution by continuous ion exclusion chromatography;

(l) concentrating the sugar containing solution to about 12–14% sugar with a reverse osmosis filter;

(m) adjusting the pH of the concentrated sugar containing solution obtained in step (l) to about 6 with ammonia;

(n) fermenting with yeast the solution obtained in step (m) at about 25° to about 36° C. to give a beer;

(o) filtering the yeast from the beer obtained in step (n); and (p) distilling the ethanol from the filtered beer obtained in step (o).

14. The method of claim 13, wherein the dried insoluble component in step (g) is admixed with sewage sludge or sewage sludge cake before treatment with said concentrated sulfuric acid.

15. A method for producing ethanol from municipal solid waste, comprising the following steps:

(a) obtaining municipal solid waste;

(b) removing tires, bulk ferrous and non-ferrous metals, plastic, glass and rubber from the waste to give a cellulosic component;

(c) shredding the cellulosic component obtained in step (b);

(d) treating the shredded cellulosic component obtained in step (c) with about 1:1 concentrated sulfuric acid to solid component, by weight, to give a partially hydrolyzed mixture;

(e) diluting the partially hydrolyzed mixture obtained in step (d) with water at a temperature of about 80° to 100° C.;

(f) agitating the diluted mixture obtained in step (e) at about 80° to 100° C. to give a digested material;

(g) removing the solids and essentially all of the heavy metals from the digested mixture obtained in step (f) to give a filtrate;

(h) separating the filtrate into an acid containing solution and a sugar containing solution;

(i) concentrating the sugar solution to about 12–14% sugar;

(j) adjusting the pH of the concentrated sugar containing solution obtained in step (i) to about 6;

(k) fermenting with yeast the solution obtained in step (j) to give a beer; and (l) recovering the ethanol from the beer obtained in step (k).

16. The method of claim 15, wherein in step (e), the partially hydrolyzed mixture obtained in step (d) is diluted with water at a temperature of about 80° to 100° C. water to give a solution containing about 4 to 6 parts water to about 1 parts partially hydrolyzed material, by weight.

17. The method of claim 15, wherein the shredded cellulosic component in step (d) is admixed with sewage sludge or sewage sludge cake before treatment with said concentrated sulfuric acid.

18. A method for removing heavy metals and producing glucose from the cellulosic component of municipal solid waste, comprising the following steps:

(a) obtaining municipal solid waste;

(b) removing tires, bulk ferrous and non-ferrous metals, plastic, glass and rubber from the waste to give a cellulosic component;

(c) shredding the cellulosic component obtained in step (b);

(d) treating the shredded cellulosic component obtained in step (c) with about 1:1 concentrated sulfuric acid to solid component at about 30° to 80° C. to give a partially hydrolyzed mixture;

(e) diluting the partially hydrolyzed mixture obtained in step (d) with water a temperature of about 80° to 100° C.;

(f) agitating the diluted mixture obtained in step (e) at about 80° to 100° C. to give a digested material; and (g) separating the insoluble component containing essentially all of the heavy metals from the soluble component obtained in step (f);

whereby an acidic solution of glucose is obtained.

19. The method of claim 18, wherein the shredded cellulosic component in step (d) is admixed with sewage sludge or sewage sludge cake before treatment with said concentrated sulfuric acid.

20. The method of claim 18, wherein the insoluble component obtained in step (g) is subjected to further treatment comprising the following steps:

(a) treating the insoluble component with about a 1 to 10% salt solution to solubilize the associated heavy metals;

(b) separating the salt solution from the insoluble component; and (c) treating the salt solution obtained in step (b) with lime to precipitate the heavy metals.

21. A method for producing ethanol from the cellulosic component of municipal solid waste comprising the following steps:

(a) shredding the cellulosic component of municipal solid waste;

(b) hydrolyzing with acid the cellulosic component in step (a) to obtain a soluble and insoluble component;

(c) separating the soluble and insoluble components obtained in step (b);

(d) separating the soluble component obtained in step (c) into an acid containing solution and a sugar containing solution by continuous ion exclusion chromatography;

(e) concentrating the sugar containing solution to about 12–14% sugar with a reverse osmosis filter;

(f) adjusting the pH of the concentrated sugar containing solution obtained in step (e) to about 6 with ammonia;

(g) fermenting with yeast the solution obtained in step (f) at about 25° to about 36° C. to give a beer;

(h) removing the yeast from the beer obtained in step (g);

(i) distilling the ethanol from the beer obtained in step (h);

(j) drying the insoluble component obtained in step (c); and (k) burning the dry insoluble component obtained in step (j) as a fuel to provide heat for the distillation of ethanol in step (i) from the filtered beer obtained in step (h).

22. The method of claim 21, wherein the cellulosic component in step (b) is admixed with sewage sludge or sewage sludge cake before hydrolyzing with said acid.

23. The process of claim 21, wherein the dry insoluble component obtained in step (j) is mixed with non-chlorinated plastic prior to burning in step (k).

24. The method of claim 1, 13 or 15, wherein the insoluble component obtained after the acid hydrolysis step is dried and burned as a boiler fuel.

25. A method for producing ethanol from an organic feedstock material, comprising the following steps:

(a) hydrolyzing with acid an organic feedstock material comprising a cellulosic component to obtain a soluble and insoluble component;

(b) separating the soluble and insoluble components obtained in step (a);

(c) separating the soluble component obtained in step (b) into an acid containing solution and a sugar containing solution by continuous ion exclusion chromatography;

(d) concentrating the sugar containing solution to about 12–14% sugar with a reverse osmosis filter;

(e) adjusting the pH of the concentrated sugar containing solution obtained in step (d) to about 6 with ammonia;

(f) fermenting with yeast the solution obtained in step (e) at about 25° to about 36° C. to give a beer;

(g) removing the yeast from the beer obtained in step (f);

(h) distilling the ethanol from the beer obtained in step (g);

(i) drying the insoluble component obtained in step (b); and (j) burning the dry insoluble component obtained in step (i) as a fuel to provide heat for the distillation of ethanol in step (h) from the beer obtained in step (g).

26. The method of claim 25, wherein the organic feedstock material comprising a cellulosic component is selected from the group consisting of cottonseed waste, switch grass, paper pulp, textile bag house residue, agricultural waste, sugar beet waste, sugar cane waste, municipal solid waste, sewage sludge and mixtures thereof.

27. The process of claim 25, wherein the dry insoluble component obtained in step (i) is mixed with non-chlorinated plastic prior to burning in step (j).

* * * * *